(12) United States Patent
Vafai et al.

(10) Patent No.: US 7,288,404 B2
(45) Date of Patent: Oct. 30, 2007

(54) MICROCANTILEVERS FOR BIOLOGICAL AND CHEMICAL ASSAYS AND METHODS OF MAKING AND USING THEREOF

(75) Inventors: Kambiz Vafai, Mission Viejo, CA (US); Cengiz Ozkan, San Diego, CA (US); Robert C. Haddon, Riverside, CA (US); Abdul-Rahim A. Khaled, Riverside, CA (US); Mo Yang, Riverside, CA (US)

(73) Assignee: Regents of the University of California, Oakland, CA (US)

( * ) Notice: Subject to any disclaimer, the term of this patent is extended or adjusted under 35 U.S.C. 154(b) by 641 days.

(21) Appl. No.: 10/422,776

(22) Filed: Apr. 25, 2003

(65) Prior Publication Data

US 2007/0141721 A1 Jun. 21, 2007

Related U.S. Application Data

(60) Provisional application No. 60/376,531, filed on Apr. 29, 2002, provisional application No. 60/411,354, filed on Sep. 16, 2002, provisional application No. 60/417,440, filed on Oct. 9, 2002.

(51) Int. Cl.
*C12M 1/34* (2006.01)
(52) U.S. Cl. .................. 435/287.1; 204/403; 204/400; 436/86; 436/164
(58) Field of Classification Search ............... 204/403, 204/400; 436/86, 164; 250/234, 225, 235; 435/287.1
See application file for complete search history.

(56) References Cited

U.S. PATENT DOCUMENTS 6,325,904 B1 * 12/2001 Peeters ...................... 257/414

OTHER PUBLICATIONS

Marie et al, Adsorption kinetics and mechanical properties of thiol-modified DNA-oligos on gold investigated by microcantilever sensors, May 2002, Ultramicroscopy, 91, 29-36.*
Bergaud et al, Finite element calculations and fabrication of cantilever sensors for nanoscale detection, Oct. 2001, Emerging Technologies and Factory Automation, 2001. Proceedings, 82, 69-77.*
Chen et al. (1994) "Resonance response of scanning force microscopy cantilevers" Rev. Sci. Instrum. 65(8):2532-2537.
Cowburn et al. (1997) "High sensitivity measurement of magnetic fields using microcantilevers" Appl. Phys. Lett. 71(15):2202-2204.

(Continued)

*Primary Examiner*—Long V. Le
*Assistant Examiner*—Nelson Yang
(74) *Attorney, Agent, or Firm*—Suzannah K. Sundby, Esq.; Smith, Gambrell & Russell, LLP

(57) ABSTRACT

Disclosed herein are microcantilevers having structural shapes that are less sensitive to turbulence and drift effects yet provide greater deflections due to analyte concentration. The structural shapes include a C-shaped microcantilever, an E-shaped microcantilever, an L-shaped microcantilever, a double microcantilever, a slit microcantilever, a tapered microcantilever, and a triangular microcantilever. The microcantilevers may be piezoresistive microcantilevers. Also disclosed are microsensors, microfludic devices, and biochips that comprise the microcantilevers as well as methods of using the microcantilevers to detect analytes in a fluid sample.

66 Claims, 26 Drawing Sheets

OTHER PUBLICATIONS

Datskos and Sauers (1999) "Detection of 2-mercaptoethanol using gold-coated micromachined cantilevers" Sensors and Actuators B 61:75-82.

Godin et al. (2001) "Quantitative surface stress measurements using a microcantilever" Appl. Phys. Lett., 79(4):551-553.

Grogan et al. (2002) "Characterisation of an antibody coated microcantilever as a potential immuno-based biosensor" Biosensors & Bioelectronics 17:201-207.

Hansen et al. (2001) "Cantilever-Based Optical Deflection Assay for Discrimination of DNA Single-Nucleotide Mismatches" Anal. Chem. 73:1567-1571.

Khaled and Vafai (2002) "Flow and heat transfer inside thin films supported by soft seals in the presence of internal and external pressure pulsations"International Journal of Heat and Mass Transfer 45:5107-5115.

Khaled and Vafai (2003) "Heat transfer and hydromagnetic control of flow exit conditions inside oscillatory squeezed thin films" Numerical Heat Transfer, Part A 43:239-258.

Khaled and Vafai (2003) "Analysis of flow and heat transfer inside oscillatory squeezed thin films subject to a varying clearance" International Journal of Heat and Mass Transfer 46:631-641.

Khaled et al. (2003) "Analysis, control and augmentation of microcantilever deflections in biosensing systems" Sensors and Actuators B 94:103-115.

Moulin et al. (1997) "Micromechanical thermal sensors: Comparison of experimental results and simulations" J. Vac. Sci. Technol. B 15(3):590-596.

Shi (2003) "Cantilever optical vibrometer using fiber Bragg grating" Opt. Eng. 42(11):3179-3181.

* cited by examiner

MICROCANTILEVERS FOR BIOLOGICAL AND CHEMICAL ASSAYS AND METHODS OF MAKING AND USING THEREOF

CROSS-REFERENCE TO RELATED APPLICATIONS

This application claims the benefit of U.S. Provisional Patent Application No. 60/376,531 filed 29 Apr. 2002, which names Kambiz Vafai, Cengiz Ozkan, and Robert C. Haddon as inventors, U.S. Provisional Patent Application No. 60/411,354 filed 16 Sep. 2002, which names Kambiz Vafai, Cengiz Ozkan, Robert C. Haddon, Abdul-Rahim A. Khaled, and Mo Yang as inventors, and U.S. Provisional Patent Application No. 60/417,440 filed 9 Oct. 2002, which names Kambiz Vafai, Cengiz Ozkan, Robert C. Haddon, Abdul-Rahim A. Khaled, and Mo Yang as inventors, all of which are herein incorporated by reference in their entirety.

BACKGROUND OF THE INVENTION

1. Field of the Invention

The present invention generally relates to microsensors for assaying analytes. In particular, the present invention relates to microcantilevers and methods of making and using thereof.

2. Description of the Related Art

The rapid growth of nanotechnology has led to new horizons for the development of microsensors that can be used to detect, measure, analyze, and monitor chemical and biological agents in samples of a few microliters or less. Microsensors can be used to detect, measure, analyze, or monitor hazardous biological and chemical agents such as organisms belonging to *Bacillus, Aycobacteriuin, Francisella, Brucella, Clostridium, Yersinia, Variola, Orthopox,* and *Burkholdleria*, toxins, chemical warfare agents, organophosphates (OPs), pesticides, insecticides, and the like in an environment. Microsensors may also be used in clinical settings to screen a patient for the presence of a disease, determine a patient's likelihood of obtaining a given disease, determine a patient's susceptibility to a given drug, and the like.

Microsensors include microfluidic devices such as biochips which comprise a collection of microarrays such as DNA or protein microarrays arranged on a solid support. An example of a biochip is the biological IC chip. See Vo-Dinh, T. et al. (2001) Nanosensors and Biochips: Frontiers in Biomolecular Diagnostics, Sensors and Actuators B 74:1560-1564.

Microsensors containing microcantilevers have been shown to be sensitive and accurate. See Wu, G., et al. (2001) Nature Biotech. 19(9):856-860. Changes in the physical properties of a microcantilever is used to detect changes in the environment of the microcantilever. Most often the deflection or conductivity of the microcantilever is measured and then used to indicate the presence or absence of a certain analyte. Microcantilevers are commonly made of silicon, silicon nitride, glass, metal, or combinations thereof.

For use in assays for biological or chemical agents, the microcantilevers are commonly a bimaterial, such as gold on one side and silicon on the other side. The gold side is then coated with a receptor that specifically binds a given ligand. Receptor/ligand pairs include antibodies and antigens, complementary nucleotide sequences, receptors and small molecules, and the like. See Raiteri, R., et al. (1999) Sensors and Actuators B 61:213-217. When the receptor binds the ligand, the side coated with the receptor will either become tensioned or relieved, thereby causing the microcantilever to deflect. The concentration of the ligand can be determined by the degree of deflection. The amount of deflection is usually in nanometer lengths that may be measured using various techniques known in the art such as optical techniques.

Unfortunately, microcantilevers are subject to turbulence in the liquid flow of samples which affects the accuracy of the measurements. See Raiteri, R., et al. (1999) Sensors and Actuators B 61:213-217, and Fritz, J., et al. (2000) Science 288:316-318. Additionally, microcantilevers in the prior art have low sensitivity especially for low analyte concentration and variations in sample temperature can produce unwanted deflections due to bimaterial effects as discussed by Fritz, J. et al. (2000) Science 288:316-318.

Conventional (non-piezoresistive) microcantilevers used along with an optical detection systems require rigorous alignment of the detecting laser beam with respect to the microcantilever position. In some cases, the laser beam is aligned to hit a shiny silicon surface or a metal coated sensing area on the back of the microcantilever. In a liquid environment, turbulence effects may result in additional three-dimensional deflections of the microcantilever beam which will render any detection measurements useless. In addition, the presence of a focused laser beam in a liquid environment can result in additional thermal effects that can result in extraneous readings.

Therefore, a need exists for microcantilevers that are highly sensitive and have low turbulence effects.

SUMMARY OF THE INVENTION

The present invention generally relates to microcantilevers for assaying analytes.

The present invention provides a microcantilever having a structural shape that has an extension length that provides a detectable characteristic when at least one given ligand is complexed with at least one receptor immobilized on at least one surface of the microcantilever that is greater than an ordinary microcantilever having the same extension length.

In some embodiments of the present invention, the microcantilever comprises two sections. In some embodiments, the first section is attached to a solid support and has a length that is shorter than the second section that is attached to the first section and forms about a 90 degree angle in the same plane as the first section. In preferred embodiments, the microcantilever is an L-shaped microcantilever. In some embodiments, the first and second sections have a top surface and a bottom surface and the receptor is immobilized on either the top surface or the bottom surface. In some embodiments, the microcantilever has an area that is less subject to drag than the ordinary microcantilever having a similar surface area. In preferred embodiments, about 10% or more, more preferably about 20% or more, even more preferably about 30% or more, more preferably about 40% or more of the area is less subject to drag. In some embodiments, the microcantilever has a thermal capacitance that is larger than the ordinary microcantilever having a similar thickness and a similar length to the second section. In preferred embodiments, the thermal capacitance of the microcantilever is about 10% or more, more preferably about 20% or more, even more preferably about 30% or more, more preferably about 40% or more of the thermal capacitance of the ordinary microcantilever.

In some embodiments, the first section is attached to a solid support and the second section is attached to the solid support and the first section and the second section are attached to each other to form a long slit having a width. In preferred embodiments, the microcantilever is a slit microcantilever. In some embodiments, the width is similar to the width of an ordinary microcantilever. In some embodiments, the first section has a top surface and a bottom surface and the second section has a top surface and a bottom surface and the receptor is immobilized on the top surface of the first section and the bottom surface of the second section and the detectable characteristic is the change in the width of the long slit. In some embodiments, the long slit has a maximum width of about 0.25 to about 0.5, preferably about 0.3 to about 0.5, more preferably about 0.4 to about 0.5 times the deflection of the ordinary microcantilever having a similar thickness and a similar slit length. In some embodiments, the width allows photons to pass through the long slit. In some embodiments, the microcantilever is affected minimally, if at all, by the presence of flow dynamical effects when compared to the ordinary microcantilever. In some embodiments, the microcantilever has a lower deflection due to flow dynamical effects than the ordinary microcantilever.

In some embodiments, the first section is attached to a solid support and the second section is attached to the solid support at a distance directly under the first section in a plane that is parallel to the plane of the first section. In preferred embodiments, the microcantilever is a double microcantilever. In some embodiments, the distance is about 1 to about 200 μm, preferably about 5 to about 100 μm, more preferably about 5 to about 50 μm, and even more preferably about 5 to about 20 μm. In some embodiments, the first section has a top surface and a bottom surface and the second section has a top surface and a bottom surface and the receptor is immobilized on the top surface of the first section and the bottom surface of the second section or the bottom surface of the first section and the top surface of the second section and the detectable characteristic is the change in the distance resulting from the deflection of the first section due to surface stress and the deflection of the second section due to surface stress. In some embodiments, the sum of the deflection of the first section and the second section is about 0.5 to about 2.0, preferably about 1.0 to about 2.0, more preferably about 1.5 to about 2.0, and most preferably about 2.0 times the deflection of the ordinary microcantilever having a similar thickness and a similar length to one section of the microcantilever. In some embodiments, the microcantilever has an area that is less subject to drag than the ordinary microcantilever having a similar thickness and a similar length to one section of the microcantilever. In some embodiments, the microcantilever has a thermal capacitance of about 0.5 to about 2.0, preferably about 1.0 to about 2.0, more preferably about 1.5 to about 2.0, and most preferably about 2.0 times the thermal capacitance of an ordinary microcantilever having a similar thickness and similar length to one section of the microcantilever.

In some embodiments of the present invention, the microcantilever comprises three sections. In some embodiments, the first section has an end attached to a solid support and the second section has an end attached to the solid support and the third section is attached to the first section and the second section at ends opposite to the ends attached to the solid support. In preferred embodiments, the microcantilever is a C-shaped microcantilever. In some embodiments, each of the sections have a top surface and a bottom surface and the receptor is immobilized on the top surfaces of the first section and the second section and the bottom surface of the third section, or on the bottom surfaces of the first section and the second section and the top surface of the third section and the detectable characteristic is the deflection of the ends of the first section and the second section that are attached to the third section and the deflection of the third section. In some embodiments, the microcantilever has a maximum deflection due to surface stress of about 0.5 to about 1.25, preferably about 1.0 to about 1.25 times the maximum deflection of the ordinary microcantilever having a similar thickness and similar length to the third section. In some embodiments, the microcantilever has an effective mass of about 0.5 to about 2.0 or more, preferably about 1.0 to about 2.0 or more, more preferably about 1.5 to about 2.0 or more, and most preferably about 2.0 or more times the effective mass related to the inertia of microcantilever of the ordinary microcantilever having a similar thickness and a similar length to the third section. In some embodiments, the microcantilever has a thermal capacitance of about 0.5 to about 3.0, preferably about 1.0 to about 3.0, more preferably about 1.5 to about 3.0, even more preferably about 2.0 to about 3.0 times the thermal capacitance of the ordinary microcantilever having a similar thickness and a similar length to the third section.

In some embodiments of the present invention, the microcantilever comprises four sections. In some embodiments, the first section has an end attached to a solid support and the second section has an end attached to the solid support and the third section is attached to the first section and the second section at ends opposite to the ends attached to the solid support and the fourth section is attached to about the middle of the third section and has a free end that extends in a direction towards the solid support. In preferred embodiments, the microcantilever is an E-shaped microcantilever. In some embodiments, each section has a top surface and a bottom surface and the receptor is immobilized on the top surfaces of the first section and the second section or on the bottom surfaces of the first section and the second section and the detectable characteristic is the deflection of the ends of the first section and the second section that are attached to the third section and the deflection of the third section. In some embodiments, the receptor is immobilized on the top surface of the third section when the receptor is immobilized on the bottom surfaces of the first section and the second section and immobilized on the bottom surface of the third section when the receptor is immobilized on the top surfaces of the first section and the second section. In some embodiments, the receptor is immobilized on the top surface of the fourth section, the bottom surface of the fourth section, or both and the detectable characteristics is the maximum deflection between the deflection of the free end of the fourth section or of the ends of the first section and the second section that are attached to the third section. In some embodiments, the microcantilever has a maximum deflection due to surface stress of about 0.5 to about 2.0, preferably about 1.0 to about 2.0, more preferably about 1.5 to about 2.0, even more preferably about 2.0 times deflection of the ordinary microcantilever having a similar thickness and a similar length to the fourth section. In some embodiments, the microcantilever has an effective mass of about 0.5 to about 2.0 or more, preferably about 1.0 to about 2.0 or more, more preferably about 1.5 to about 2.0 or more, and most preferably about 2.0 or more times the deflection of the ordinary microcantilever having a similar thickness and similar length to the fourth section. In some embodiments, the microcantilever has a thermal capacitance that is about 0.5 to about 3.0, preferably about 1.0 to about 3.0, more preferably about 1.5 to about 3.0, even more preferably about 2.0 to about 3.0 times the thermal capacitance of the ordinary microcantilever having a similar thickness and a similar length to the fourth section. In some embodiments, the microcantilever has a lower deflection due to flow dynamical effects than the ordinary microcantilever.

In some embodiments of the present invention, the microcantilever has an end that is attached to a solid support and a free end that extends from the solid support and the end attached to the solid support has a base width that is wider than the free end. In preferred embodiments, the microcantilever is a triangular microcantilever or a tapered microcantilever. In some embodiments, the microcantilever has an area that is less subject to drag than the ordinary microcantilever having a similar length and a similar base width.

In some embodiments of the present invention, the microcantilever has a piezoresistive layer and the detectable characteristic is the change in piezoresitivity. In some embodiments, the microcantilever is attached to a solid support and the piezoresistive layer is located on the microcantilever in an area near the solid support. In some embodiments, the microcantilever may further comprise at least one stress concentrated region. The stress concentrated region may be the result of at least one hole in the microcantilever. The hole may be located in the area near the solid support.

In some embodiments, the microcantilevers of the present invention further comprise at least one nanostructure attached thereto. The nanostructure may be a nanotube, a nanobead, a nanocrystal, a quantum bead, a quantum dot, or a colloid. In some embodiments, the nanostructure may be functionalized.

In some embodiments, the present invention provides a method for assaying at least one analyte in a fluid sample which comprises exposing at least one of the microcantilevers of the present invention to the fluid sample and detecting or measuring the detectable characteristic of the given microcantilever. In some embodiments, the analyte is a chemical agent or a biological agent. In some embodiments, the chemical agent is an insecticide, a pesticide, a herbicide, tabun, sarin, soman, methylphosphonothioic acid, sulphur mustard, nitrogen mustard, lewisite, phosgene oximine, phosgene, diphosgene, chloropicrin, an organophosphate compound, or the like. In some embodiments, the biological agent is a cellular receptor, a peptide, a polypeptide, a protein, an antibody, an antigen, a polynucleotide, a polysaccharide, a lipid, a steroid, a prostaglandin, a toxin, a prostacycline, or the like. In some embodiments, the toxin is a botulinum toxin, a ricin toxin, a saxitoxin, an enterotoxin, an exotoxin, a mycotoxin, a neurotoxin, or the like. In some embodiments, detection of the biological agent is indicative of the presence of an organism belonging to *Bacillus, Mycobacterium, Francisella, Brucella, Clostridium, Yersinia, Variola, Orthopox*, or *Burkholderia* or a virus that causes Congo-Crimean hemorrhagic fever (CCHF), Ebola Haemorrhagic Fever, Rift Valley Fever (RVF), smallpox, or Venezuelan equine encephalitis (VEE). In some embodiments, the fluid sample is a liquid, a suspension, or a gas. In some embodiments, the detectable characteristic is the deflection of the microcantilever, the piezoresistance of the microcantilever, the surface stress of the microcantilever, the resonance frequency of the microcantilever, or a combination thereof. In some embodiments, the method further comprises contacting at least one nanostructure having at least one receptor for the ligand complexed with the receptor immobilized to the surface of the microcantilever. The nanostructure may be a nanotube, a nanobead, a nanocrystal, a quantum bead, a quantum dot, or a colloid. In some embodiments, the nanostructure may be functionalized.

In some embodiments, the present invention provides a device comprising at least one microcantilever of the present invention. In some embodiments, the device may comprise a plurality of microcantilevers. The device may further comprise at least one microchannel through which a fluid sample may flow. The device may further comprise at least one chamber. In some embodiments, the chamber comprises the microcantilever. In some embodiments, the chamber comprises at least one reagent required for detecting or measuring the ligand.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1 is an electron micrograph of a 200-μm long silicon microcantilever obtained from www1.zyvex.com/TEXMEMS3/Abstracts/microcantilever.html.

FIG. 2 is an illustration of the model system used for the analysis of analyte-receptor binding.

FIG. 3 shows the distribution of analyte concentration at t=5 seconds.

FIG. 4 shows the distribution of analyte concentration at t=60 seconds.

FIG. 5 shows the effects of $$\kappa \text{ on } \frac{(z_d)_\kappa}{(z_d)_{\kappa=0}}.$$

FIG. 6 shows the effects of $$\kappa \text{ on } \left(\frac{u}{V_o}\right)\frac{1}{(Y/H)}.$$

FIG. 7 shows the effects of $$\kappa \text{ on } \left(\frac{v}{V_o}\right)\frac{1}{(Y/H)^2}.$$

FIG. 8 shows the effects of $$\omega \text{ on } \frac{z_s}{z_o}.$$

FIG. 9 shows the effects of $$\omega \text{ on } \frac{|z_t|}{\beta_T \Delta T_\infty}.$$

FIG. 10 shows the effects of $\omega$ on $\frac{z_d}{z_o}$.

DETAILED DESCRIPTION OF THE INVENTION

Figure 1:
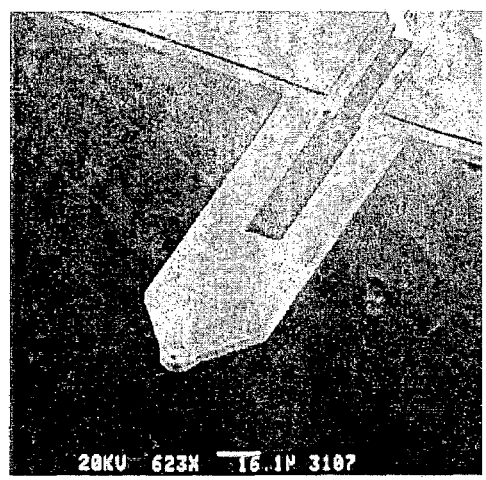

The present invention provides microcantilevers that may be used in methods and devices for detecting, measuring, monitoring, or analyzing low concentrations of at least one analyte in a fluid sample. In particular, the present invention provides microcantilevers upon which a specific binding agent may be immobilized for use in methods and devices for assaying ligand, present in a fluid sample, that specifically binds the specific binding agent.

As used herein, "assaying" is used interchangeably with "detecting", "measuring", "monitoring" and "analyzing". As used herein, a "fluid sample" refers to a continuous amorphous substance that tends to flow and to conform to the outline of a container such as a liquid or a gas. Fluid samples include blood, plasma, urine, bile, breast milk, semen, water, liquid beverages, air, and the like. If one desires to test a solid sample for a given analyte according to the present invention, the solid sample may be made into a fluid sample using methods known in the art. For example, a solid sample may be dissolved in an aqueous solution, ground up or liquefied, dispersed in a liquid medium, and the like. Alternatively, the surface of the solid sample may be tested by washing the surface with a solution such as water or a buffer and then testing the solution for the presence of the given analyte.

As used herein, a "specific binding agent" is used interchangeably with a "receptor" and refers to an agent that specifically interacts or binds with a ligand. As used herein, a "ligand" is used interchangeably with an "analyte" and refers to an atom, molecule, or ion that binds or interacts with a given receptor to form a complex. Depending on the chemistry, the receptor/ligand interaction may be reversible or irreversible. The extent of the binding depends on the affinity of the ligand to the receptor for chemical reaction, or to the chemical potential of the system. In the presence of multiple ligands and receptors, the binding can be competitive (different ligands compete for the same receptor) or non-competitive (each ligand binds to a different receptor). The affinity between each individual receptor/ligand complex determines the partitioning of total receptor sites in a competitive binding environment.

The specific binding agent can be immobilized in a manner that provides qualitative analysis of the analytes complexed with the specific binding agent. See e.g. O'Brien, J., et al. (2000) Anal. Chem. 72:703, which is incorporated herein by reference. Common receptors and ligands include cellular receptors, peptides, polypeptides, proteins, antibodies, antigens, polynucleotides, polysaccharides, lipids, steroids, prostaglandins, prostacyclines, organic molecules, combinations thereof, and the like.

The microcantilevers of the present invention may be used for medical applications such as assays for cancer, abnormal levels of certain biomolecules, abnormal biomolecules, specific nucleic acid sequences, specific antibodies, toxins, and the like in subjects. The microcantilevers of the present invention may be used for environmental applications such as assays for insecticides, pesticides, herbicides, toxins, bacteria, and the like in bodies of water and the air. The microcantilevers of the present invention may used to assay for chemical and biological agents that may be used in biochemical warfare such as organisms belonging to *Bacillus, Mycobacterium, Francisella, Brucella, Clostridium, Yersinia, Variola, Orthopox*, and *Burkholderia*, viruses such as those that cause Congo-Crimean hemorrhagic fever (CCHF), Ebola Haemorrhagic Fever, Rift Valley Fever (RVF), smallpox, and Venezuelan equine encephalitis (VEE), toxins such as botulinum toxins, ricin toxin, saxitoxin, enterotoxins, exotoxins, mycotoxins, and neurotoxins, tabun, sarin, soman, methylphosphonothioic acid, sulphur mustard, nitrogen mustard, lewisite, phosgene oximine, phosgene, diphosgene, chloropicrin, organophosphates (OPs), pesticides, insecticides, and the like. Various known receptors or specific binding agents that are known to specifically bind given analytes such as the analytes referenced above may be used.

The microcantilevers of the present invention have structural shapes that are different from prior art microcantilevers such that the structural shapes of the microcantilevers increase detectable characteristics such as deflections due to the presence of analytes which thereby increases sensitivity, yet reduces the influence of turbulence and drift effects on deflections which thereby increases accuracy. All or part of a microcantilever of the present is correlated to a prior art microcantilever in order to compare their mechanical, chemical, and electrical properties. For example, when comparing the maximum deflections due to surface stress of a C-shaped microcantilever provided herein and an ordinary microcantilever, the prior art microcantilever is to have a similar thickness and a similar length to the third section of the C-shaped microcantilever. The term "similar" as used in this context herein, refers to less than about 10%, preferably less than about 5%, more preferably less than about 2.5%, even more preferably less than about 1%, and most preferably less than about 0.5% difference.

A prior art microcantilever is shown in FIG. 1. As used herein, "prior art microcantilever" and "ordinary microcantilever" are used interchangeably to refer to microcantilevers that are known in the art. Ordinary microcantilevers include those having the general shape set forth in FIG. 1. Ordinary microcantilevers also include those having a shape that is generally rectangular and may further have a rounded free end or an end as shown in FIG. 1. The deflection (z) of the tip of the ordinary microcantilever can be calculated using the following equation:

$$Z = \frac{3l^2(1-v)}{Et^2}\Delta\sigma \quad (1)$$

wherein
 l is the effective length of the microcantilever,
 v is Poisson's ratio,
 E in Young's modulus,
 $\Delta\sigma$ is differential surface stress,
 t is the microcantilever thickness.

See Lavrik, N. V., et al. (2001) Biomedical Microdevices 3(1):35-44, which is herein incorporated by reference.

Deflection Due to Surface Stresses

The differential surface stress, $\Delta\sigma$, is proportional to the number of analytes bound to receptors immobilized on the surface of the microcantilever. This relation is as follows:

$$\Delta\sigma = \Delta G \Gamma M^{-1} \quad (2)$$

wherein
 $\Delta G$ is the change in the Gibbs free energy caused by the adsorption process,
 $\Gamma$ is the mass of the bound analyte molecules per unit area, and
 M is the molar mass of the analyte.

See Lavrik, N. V., et al. (2001) Biomedical Microdevices 3(1):35-44, which is herein incorporated by reference. This equation is based on the Dupre equation that relates the surface free energy of the solid support and the adsorbate and the work of adhesion.

Rate of Reaction

The first order chemical reaction equation is as follows:

$$\frac{dN_b}{dt} = k_{ad}(N_o - N_b) \quad (3)$$

wherein
 $k_{ad}$ is the adhesion rate,
 $N_b$ is the cumulative number of bound cells, and
 $N_o$ is the total number of cells bound on the solid support after the experiment.

The adhesion rate according is $$k_{ad} = k_f C_\infty N_r \quad (4)$$

wherein
 $k_f$ is the effective reaction rate,
 $C_\infty$ is the surface analyte concentration, and
 $N_r$ is the number of available receptors.

See Chang and Hammer (1999) Biophysical Journal 76:1280-1292, which is herein incorporated by reference.

The results of Swift, D. G., et al. (1998) agrees with the previous equation. See Biophysical Journal 75:2597-2611, which is herein incorporated by reference. Thus, Equation (3) reduces to following:

$$\frac{dN_b}{(N_o - N_b)} = k_f C_\infty N_r dt \quad (5)$$

The analyte concentration due to turbulence can be expressed as follows:

$$C_\infty = (C_\infty)_o - \beta_c \sin(\omega t) \quad (6)$$

wherein ($C_\infty)_o$ is the mean free stream analyte concentration, and
$\beta_c$ is the amplitude of concentration.

$k_f$ increases with the vibrational frequency of the molecules. See Chang and Hammer (1999). Also, the turbulence at the surface of the microcantilever which is produced by the varying surface roughness due to the presence of immobilized receptors results in an increase in the effective reaction rate at the surface of the microcantilever. The increase in the effective reaction rate is due to the mixing effect that the turbulence produces which increases the vibrational frequency of the molecules. See Ramakrishnan and Sadana (2000) J. of Interface and Colloid Science 229:628-640, which is herein incorporated by reference. Turbulence at the receptor surface can also be produced by disturbances in the flow of the fluid sample being tested.

For simplicity, the relation between the effective reaction rate and the turbulence frequency is taken to be linear as follows:

$$k_f = \overline{k}_f(1+a\omega) \quad (7)$$

wherein $\overline{k}_f$ is the effective reaction rate in the absence of the turbulence, and
a is a constant.

Thus Equation (5) reduces to:

$$\frac{dN_b}{(N_o - N_b)} = \overline{k}_f(1+a\omega)[(C_\infty)_o - \beta_c \sin(\omega t)]N_r dt \quad (8)$$

This is a first order differential equation and has the following solution given that $N_b(t=0)=0$:

$$N_b = N_o\left[1 - e^{-\overline{k}_f N_f(1+a\omega)\left((C_\infty)_o t + \frac{\beta_c}{\omega}(\cos(\omega t)-1)\right)}\right] \quad (9)$$

The parameter $N_b$ can be related to $\Gamma$ by the following relation:

$$\frac{N_b}{A_m} = \Gamma M^{-1}A \quad (10)$$

wherein $\Gamma$ is the mass of the adsorbate per unit area,
M is the molar mass,
A is number of analyte molecules per mole, and
$A_m$ is the area of the receptor coating.

Therefore, the time history for the surface stress can be related to Equation (9) by applying Equations (2) and (10) and the result is:

$$\Delta\sigma = (\Delta\sigma)_o\left[1 - e^{-\overline{k}_f N_f(1+a\omega)\left((C_\infty)_o t + \frac{\beta_c}{\omega}(\cos(\omega t)-1)\right)}\right] \quad (11)$$

wherein $(\Delta\sigma)_o = \Delta G N_o A_m^{-1} A^{-1}$.

Thus, $$Z_s = Z_o\left[1 - e^{-\overline{k}_f N_f(1+a\omega)\left((C_\infty)_o t + \frac{\beta_c}{\omega}(\cos(\omega t)-1)\right)}\right] \text{ wherein } z_o = \quad (12)$$

$$\frac{3l^2(1-\nu)}{E t_m^2}(\Delta\sigma)_o.$$

It was found that the adhesion rate is inversely proportional to the translational velocity, u, of the analytes for wide range of translational velocities. The effective binding rate can be linearly correlated to the analyte rolling velocity and the translational velocity, such that:

$$\overline{k}_f = \overline{k}_{fo} - b|u| \quad (15)$$

wherein $\overline{k}_{fo}$ and b are constants greater than zero. See Pritchard, W. F., et al. (1995) J. of Biomechanics 28:1459-1469, which is herein incorporated by reference.

Therefore, Equation (12) is further reduced to:

$$Z_s = Z_o\left[1 - e^{-(\overline{k}_{fo}-b|u|)N_r(1+a\omega)\left((C_\infty)_o t + \frac{\beta_c}{\omega}(\cos(\omega t)-1)\right)}\right] \quad (14)$$

When u is greatly dependent on the time, the solution to Equation (5) is:

$$Z_s = Z_o\left[1 - e^{-\int_0^t (\overline{k}_{fo}-b|u|)N_r(1+a\omega)((C_\infty)_o - \beta_C \sin(\omega t))dt}\right] \quad (15)$$

Chemo-Mechanical Binding Analysis

A finite element computational model for simulating the chemo-mechanical binding of ligands to specific binding agents on functionalized surfaces of solid supports using CFDRC™ (Computational Fluid Dynamics Research Corporation, Sunnyvale, Calif.) is provided herein. As used herein, "functionalized" refers to a chemical modification that prepares a surface of a solid support for subsequent chemical interaction by attaching or creating suitable functional groups or moieties. For example, a support surface that does not already have desired functional groups may be treated to provide the functional groups on its surface. For example, a polystyrene support may be reacted with sulfuric acid to give a sulfonated surface that may be subjected to a subsequent chemical reaction. Assays known in the art may be used to determine the concentration of accessible functional groups on the surface after functionalization.

Figure 2:
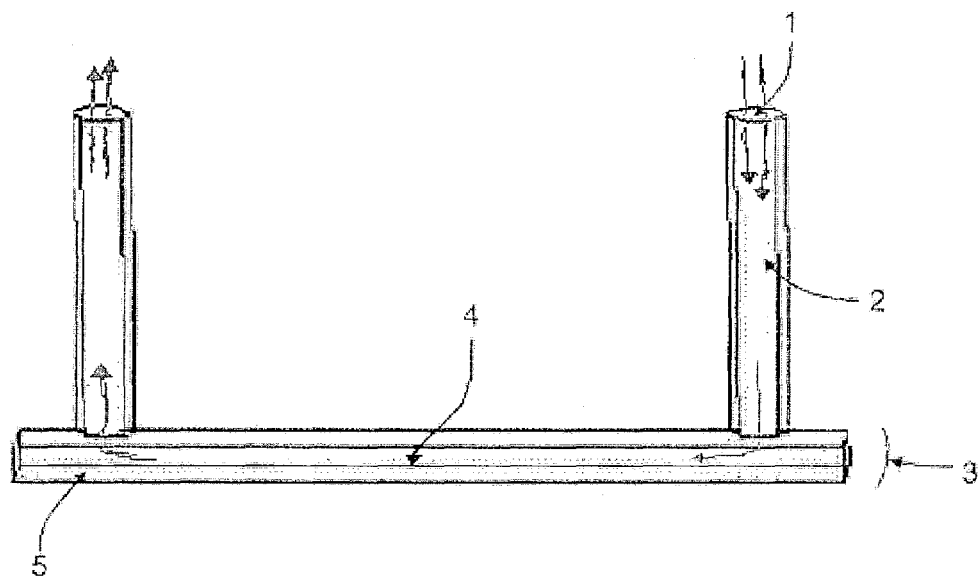

Generally, simulations were conducted on a model comprising a support functionalized with a specific binding agent inserted in a thin plate-shaped flow cell. FIG. 2 is a schematic illustration of the simulation model. As shown in FIG. 2, a fluid sample containing the analyte passes through an orifice 1 with a circular inlet port 2 connecting to a flow cell 3. A functionalized support surface 4 (such as a gold-coated glass-slide) on which the specific binding agents are attached is located in the bottom 5 of the flow cell 3. For simulations, an arbitrary set of ligands and specific binding agents having strong binding affinities were assumed. As provided in Table 1, the initial ligand concentration in the fluid sample was taken to be $5\times10^6$ M, and the inlet volumetric flow rate was 300 μl/min.

TABLE 1

Various parameters used in the chemo-mechanical binding analysis

| Property | Value |
| --- | --- |
| Association rate constant: Ka | $1 \times 10^{+9}$ $M^{-1}s^{-1}$ |
| Dissociation rate constant: Kd | $0.001$ $s^{-1}$ |
| Initial Analyte concentration in bulk solution: Co | $5 \times 10^{-6}$ M |
| Maximum possible surface analyte concentration: Ps | $2 \times 10^{-6}$ $mol/m^2$ |
| Density of sample | $1000$ $kg/m^3$ |
| Viscosity of sample | $0.86 \times 10^{-6}$ $m^2/s$ |
| Diffusivity of analyte $D_e$ | $4 \times 10^{-7}$ $cm^2/s$ |
| Inlet volumetric flow rate: Q | $300$ μl/min |

For the modeling experiments described herein, the ligand binds to its receptor to form a reversible receptor/ligand complex having an association rate constant, $K_a$, which dissociates with a rate constant, $K_d$, and can form an immobilized complex with a rate constant, $K_r$, as follows:

$$A + B \underset{K_d}{\overset{K_A}{\rightleftarrows}} AB \overset{K_r}{\longrightarrow} AB^*$$

Figure 3:
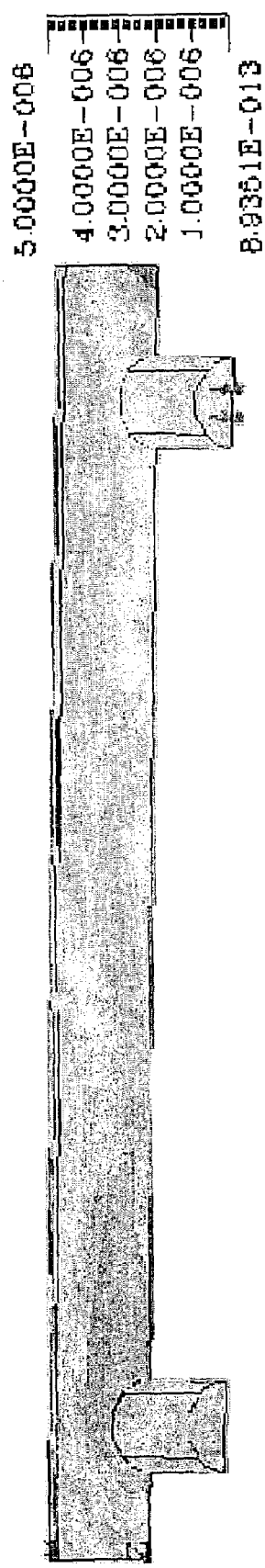
Figure 4:
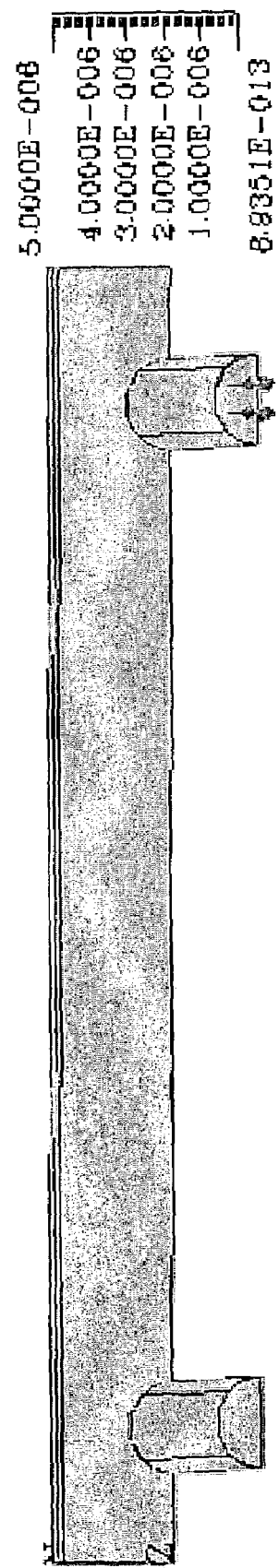

The distribution of ligand concentration over the reaction surface of the microcantilever as a function of time is illustrated in FIGS. 3 and 4. As shown in FIG. 4, after a given time, when the ligand concentration reaches a saturated level, the binding reaches a state of dynamic equilibrium. At dynamic equilibrium, the concentration of the receptor/ligand complexes is uniformly distributed over the reaction surface. Thus, stable chemo-mechanical binding provides a uniform distribution of surface stress over the microcantilever, thereby allowing the microcantilever to be used in a microsensor to detect, measure, or analyze ligands in a fluid sample.

Deflection of the Microcantilever Due to Bimaterial Effects

In a bimaterial microcantilever comprising a first layer of a material and a second layer of a different material, the temperature of the fluid sample near the microcantilever is expected to vary sinusoidally with amplitude of $\Delta T_\infty$ due to oscillations in the flow conditions. Therefore, the thermal lumped analysis predicts the following for the deflection of the microcantilever due to bimaterial effects, $Z_t$:

$$z_1 = \beta_T m \Delta T_\infty \frac{m\sin(\omega t) - \omega\cos(\omega t)}{m^2 + \omega^2} \tag{16a}$$

wherein $\beta_T$ is a constant depending on the thermal expansion coefficient of the two layers of the microcantilever and the relative dimensions of these layers.

The parameter m is equal to

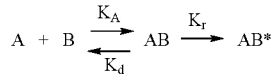

(16b)

wherein
  $h_c$ is the convective heat transfer coefficient between the microcantilever and the fluid, w is the width of the microcantilever,
  $c_m$ is the specific heat of the microcantilever, and
  $m_m$ is the total mass of the microcantilever.

Equation 16(a) suggests that bimaterial effects can be minimized for conditions where m is very small, such as for minimum heat transfer convection or for maximum thermal capacitance of the microcantilever.

Dynamic Modeling of the Microcantilever

The one degree of freedom model that can best describe the dynamic behavior of the deflection at the tip of the microcantilever, $z_d$, due to flow turbulences is shown in the following differential Equation (17):

$$m_e \ddot{z}_d + k_e z_d = \frac{1}{2} C_D \rho_1 A_e (h_o \omega F_V)^2 \sin(\omega t) \tag{17}$$

wherein
  $m_e$ is the effective mass of the microcantilever,
  $k_e$ is the effective stiffness,
  $A_e$ is the effective area of the microcantilever that are subject to flow drag,
  $F_V$ is a velocity correction factor which is the ratio between the magnitude of the velocity at the microcantilever to the velocity magnitude at the source of disturbance which is assumed to be ($h_o\omega$),
  $h_o$ is the characteristic length for the turbulence at its source,
  $C_D$ is the drag coefficient, and
  $\rho_1$ is the density of the fluid.

The double dot sign represents the second derivative with respect to time. The right side of Equation (17) represents the drag force excreted by the flow of the fluid on the microcantilever due to oscillating effects. The drag coefficient, $C_D$, depends on the geometry of the microcantilever and the direction of the flow with respect to the microcantilever.

The steady periodic solution for Equation (17) is:

$$z_d = \frac{\left(\frac{m_e}{k_c}\omega^2\right)}{1 - \frac{m_e}{k_e}\omega^2} \frac{0.5\rho_1 A_e (h_o F_V)^2 C_D}{m_e} \sin(\omega t) \tag{18}$$

Equation (18) suggests that the main parameters that control the dynamical effects are: $C_D$, $F_V$, $$\omega/\omega_n (\omega_n = k_e/m_e), \frac{\rho_1 A_e h_o}{m_e}.$$

A decrease in any of these parameters reduces the deflection due to dynamical effects.

Effects of Turbulence Produced by External Squeezing

A microfluidic cell comprising a thin film having linearly varying clearance was used to analyze flow turbulences that are produced by external noise at the upper plate of the microfluidic cell. The lower plate of the microfluidic cell was assumed fixed and horizontal while the upper plate was inclined and its vertical motion due to the external noise was assumed to have sinusoidal behavior according to the following relation:

$$h = h_o\left(1 - \delta\cos(\gamma\tau) + \kappa\frac{x}{B}\right) \quad (19)$$

wherein
   $h_o$ is the reference thickness of the fluidic cell,
   $\kappa$ is the dimensionless slope of the thin film,
   $\delta$ is the upper plate motion amplitude,
   $\tau$ is the dimensionless time ($\tau=\omega t$),
   B is the channel length,
   $\omega$ is a reference vibrational frequency,
   $\gamma$ is dimensionless frequency, and
   x is the horizontal distance starting from the inlet.

The velocity field, the horizontal dimensionless component, U, and the vertical dimensionless component, V, for the fluid flow inside a fluidic microchannel is shown below which was derived using the reduced continuity equation and Navier Stokes equations for creep flows:

$$U(X, Y, \tau) = \frac{u}{(V_o + \omega B)} = \frac{1}{2H}[S\delta\gamma X\sin(\gamma\tau) - (12 - S)]\left(\frac{Y}{H}\right)\left(\frac{Y}{H} - 1\right) \quad (20)$$

$$V(X, Y, \tau) = \quad (21)$$

$$\frac{v}{h_o\omega} = \delta\gamma\sin(\gamma\tau)\left[3\left(1 - \frac{2\kappa X}{H}\right)\left(\frac{Y}{H}\right)^2 - 2\left(1 - \frac{3\kappa X}{H}\right)\left(\frac{Y}{H}\right)^3\right] - 6\left(\frac{12}{S} - 1\right)\frac{\kappa}{H}\left[\left(\frac{Y}{H}\right)^3 - \left(\frac{Y}{H}\right)^2\right]$$

wherein
   u is dimensional axial velocity,
   v is dimensional normal velocity,
   X is the dimensional axial distance starting from the inlet normalized by B,
   Y the dimensional normal distance starting from the lower plate normalized by $h_o$, and
   $V_o$ is a reference inlet velocity.

Equations (20) and (21) are based on the assumption that the flow rate is constant at the inlet. H is equal to $h/h_o$ while S is the squeezing number which is defined by the following Equation (22):

$$S = \frac{12}{1 + \frac{V_o}{\omega B}} \quad (22)$$

wherein the flow rate at the inlet is equal to $V_o h_o$.

When a microcantilever is placed near the lower plate, $Y/H \approx 0$, then Equations (20) and (21) reduce to the following at the exit of the microchannel:

$$U(Y, \tau) = -\frac{1}{2H}[S\delta\gamma\sin(\gamma\tau) - (12 - S)]\left(\frac{Y}{H}\right) \quad (23)$$

$$V(Y, \tau) = \left[3\delta\gamma\sin(\gamma\tau)\left(1 - 2\left(\frac{\kappa}{H}\right)\right) - 6\left(\frac{12}{S} - 1\right)\left(\frac{\kappa}{H}\right)\right]\left(\frac{Y}{H}\right)^2 \quad (24)$$

Equation (24) suggests that $F_V$ can be approximated for a fluidic cell having an inclined clearance and having a microcantilever placed near the fixed plate by the following Equation (25):

$$F_V \approx 3\left(1 - 2\left(\frac{\kappa}{H}\right)\right)\left(\frac{Y}{H}\right)^2 \quad (25)$$

Therefore, the ratio of the deflection of the microcantilever due dynamical effects, $Z_d$, for an inclined microchannel to that for a flat microchannel can be approximated for lower amplitudes of the upper plate's vibrations by the following Equation (26):

$$\frac{(z_d)_\kappa}{(z_d)_{\kappa=0}} \approx \left(\frac{1-\kappa}{1+\kappa}\right)^2 \quad (26)$$

Figure 5:
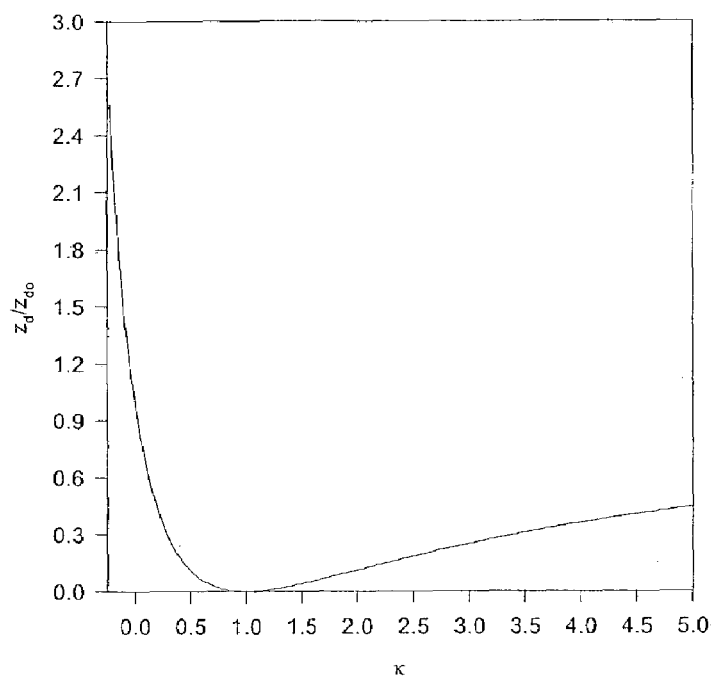

Equation (26) suggests that dynamical effects on the microcantilever deflection can be reduced for divergent fluidic cells. However, this reduction is prominent near $\kappa=1$ at relatively low values of $\delta$ as shown in FIG. 5. Furthermore, inclined microchannels create a permanent drag on the microcantilever because the mean flow will have normal velocity components, the second term in Equation (24). However, the reduction in the dynamical effects is greater than the deflection due to the induced permanent drag.

Typical Values of the Parameters

Typical values of the parameters specifying the microcantilever deflection are provided in Table 2.

TABLE 2

Typical values of the parameters specifying the microcantilever deflection

| Material | Properties<br>$Si_3N_4$ coated with thin layer of Gold |
|---|---|
| l, w, $t_m$ | 120 μm, 40 μm, 50 nm |
| $m_m$, $m_e$ | 5.59 ($10^{-13}$) kg, 1.34 ($10^{-13}$) kg |
| $k_e$, $\rho$, $(C_\infty)_0 N_r$ | 0.06 N/m, 2330 kg/m$^3$, 410 1/μm$^2$ |
| $z_0$, $h_0$, B | 50 nm, 0.4 mm, 70 mm |
| $\delta$, $\beta_c$ $N_r$ | 0.3, 82 1/μm$^2$ |
| $h_0$, $F_v$, Y/H, $V_0$ | 0.2 mm, 0.2, 0.1, 0.05 m/s |
| $\overline{k}_{fo}$, a | 17.1 ($10^{-5}$) μm$^2$/s, 0.1 s |
| m, κ | 100 s$^{-1}$, 0.0 (unless stated) |
| $C_D$, $\rho_l$, $A_e$ | 1.0, 800 kg/m$^3$, 0.5 (l w) |

The data for $(C\infty)_o N_r$, $\beta_c N_r$, and $\overline{k}_{fo}$ are extracted from the work of Chang and Hammer (1999) which shows the adhering of lymphoid cells CD8 molecules into anti-CD8-coated surface by a shear flow. The parameters a and b were assumed due to lack of experimental values.

Figure 6:
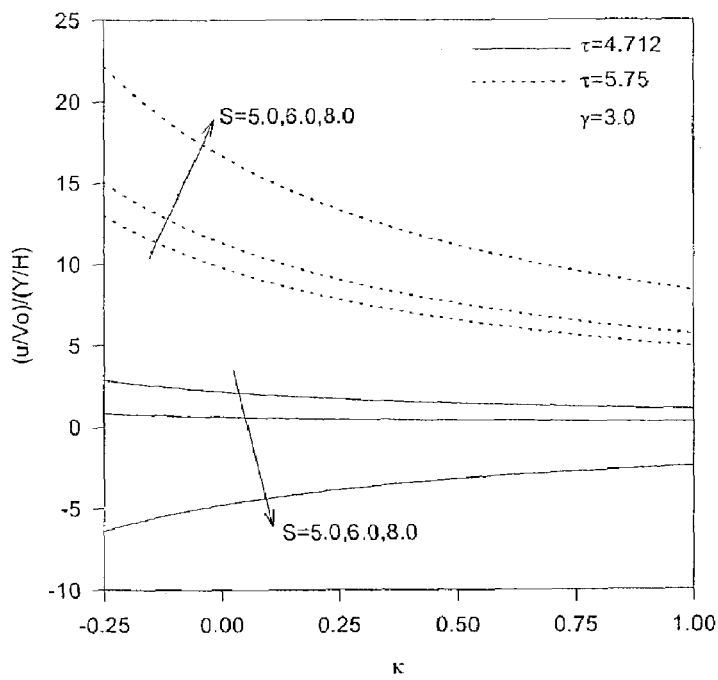
Figure 7:
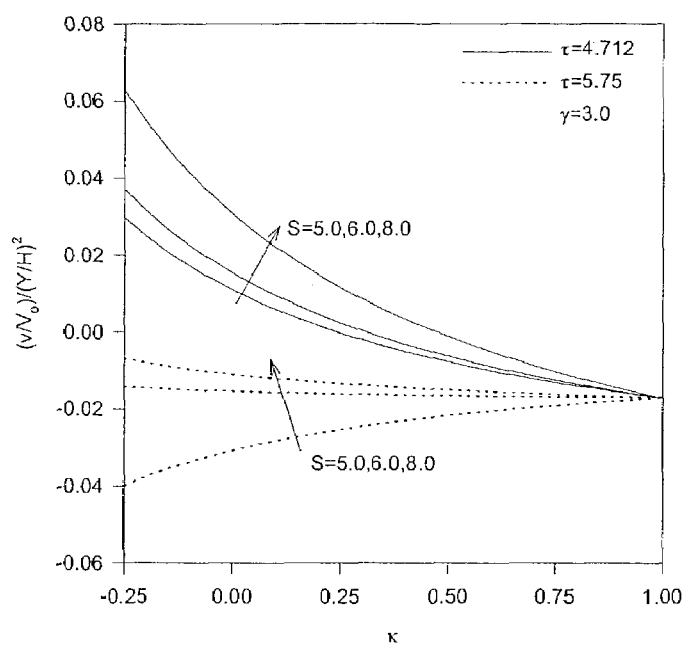

FIGS. 6 and 7 describe the effects of the dimensionless slope, κ, on translational and normal velocities, normalized with respect to $V_o$, at the exit for two different times, respectively. The effects are based on the fact that the microcantilever is placed near the lower plate in the presence of an external sinusoidal noise at the upper plate. The values of $\tau=4.712$ and $\tau=5.75$ represent the cases when the upper plate reaches its maximum relief and squeezing speeds, respectively. The absolute value of the translational velocity decreases with increases in the dimensionless slope, K, thereby increasing the adhesion rate. Increases in the squeezing number, S, can cause reductions and enhancements in rolling velocities during relief (as long as the flow is not reversed) and squeezing stages, respectively. The squeezing number, S, increases by increases in the turbulence frequency. Variations in normal velocities decrease as K increases as shown in FIG. 7.

Figure 8:
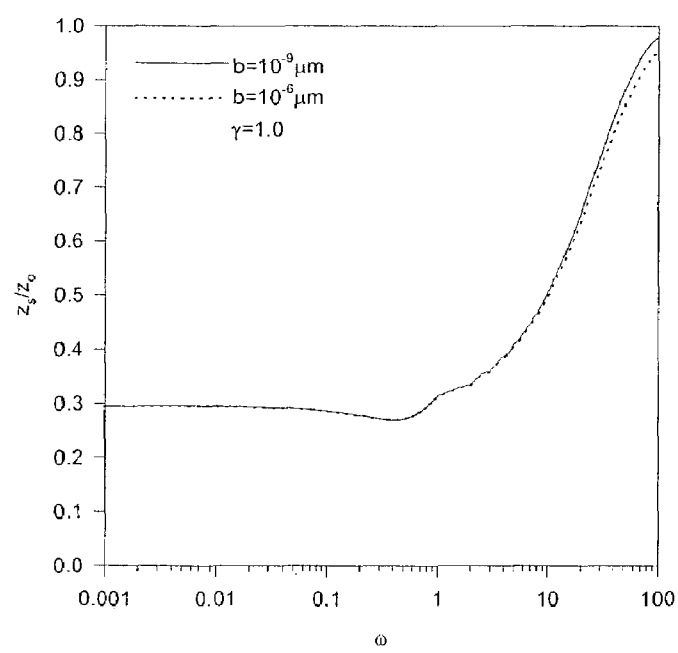
Figure 9:
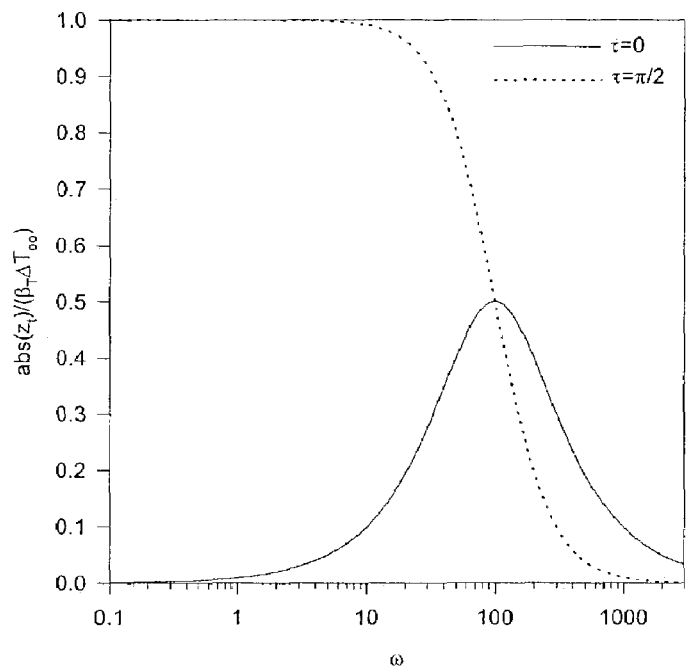

FIG. 8 shows the deflection spectrum of the microcantilever due to surface stress. The deflection at relatively small values of ω is mainly influenced by the noise in the analyte concentration near the microcantilever. In this region, the noise in the deflection spectrum is clearly recognized as shown in FIG. 8. At large values of ω, the deflection is found to increase smoothly until reaching an asymptotical value for the selected parameters. This behavior is mainly due to increases in the vibrational frequency of the analyte molecules as ω increases when the effects of the rolling velocities on the binding are small, otherwise the deflection will decrease. The spectrum for the intermediate region of ω contains small noise levels due to the interference between the effect of the noise in the concentration and vibrational/rolling effects of the analyte molecules. Decreases in the deflection are noticed as b increases due to increases in the rolling velocity effects. At relatively large frequencies, bimaterial effects on the deflection decreases as shown in FIG. 9.

Figure 10:
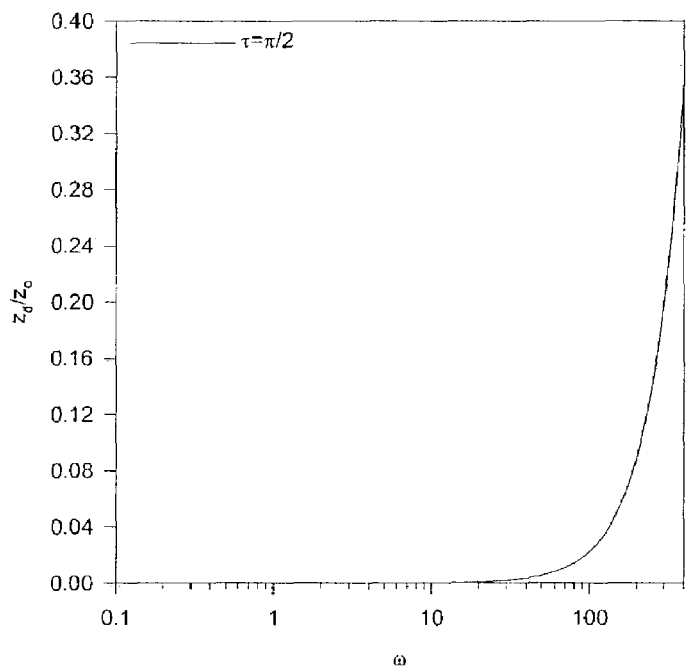

Although, the deflection of the microcantilever is enhanced at large frequencies, the noise due to dynamical disturbances on the microcantilever increases drastically as shown in FIG. 10. With regards to bimaterial effects, the produced noise can be reduced by geometrical considerations for the chamber such as using convergent chambers or using special coolers as in the works of Wu, G., et al. (2001) PNAS USA 98:1560-1564, which is herein incorporated by reference. This reduction can also be accomplished by comparing the deflection of the microcantilever with an idle one to eliminate these effects as illustrated in the work of Fritz, J., et al. (2000) Science 288:316-318, which is herein incorporated by reference.

Prior art methods of increasing deflections of ordinary microcantilevers generally included increasing the effective lengths of the microcantilevers, decreasing the thickness of the microcantilevers, or both. However, as explained above, increasing the effective length of an ordinary microcantilever and/or decreasing the thickness of the microcantilever will increase the turbulence effects on the microcantilever.

Rather than increasing the effective length or decreasing the thickness of ordinary microcantilevers, the present invention provides microcantilevers having novel structural shapes that are less sensitive to turbulence and drift effects and provide greater deflections when compared with prior art microcantilevers. Therefore, the microcantilevers of the present invention can be used to detect and measure concentrations of analytes that cannot be detected or measured by prior art microcantilevers due to their limits of detection and quantification. Since turbulence and drift effects are minimized, the microcantilevers of the present invention provide greater accuracy over prior art microcantilevers.

The various structural shapes of the microcantilevers of the present invention are provided in FIGS. 11A-11I.

A. C-Shaped Microcantilever

Figure 11A:
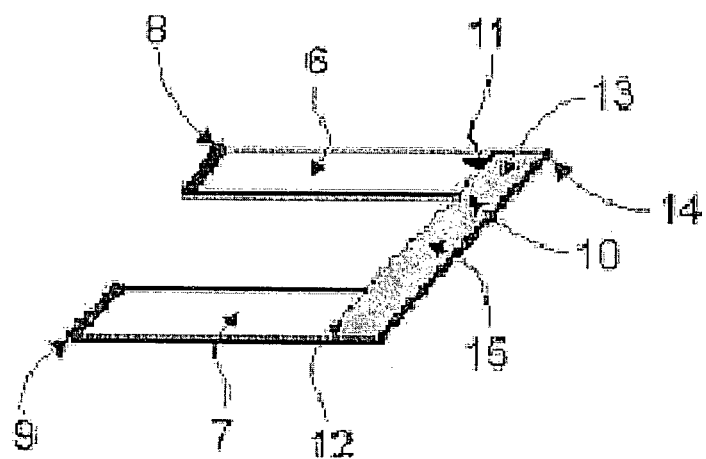
FIG. 11A is a C-shaped microcantilever.

FIG. 11A shows a diagram of a microcantilever having a "C" shape. The C-shaped microcantilever comprises two sections 6 and 7 that are attached to a support at ends 8 and 9, and a third section 10 that connects the two sections 6 and 7 at ends 11 and 12. The three sections may be synthesized as one structure or synthesized as three separate structures that are then connected together. Each section has a top surface 13 and a bottom surface 14. When used in an assay for detecting, measuring, or analyzing an analyte, a receptor R for the analyte may be immobilized on the top surfaces of the two sections 6 and 7 and then immobilized on the bottom surface of the third section 10. Alternatively, the receptor R may be immobilized on the bottom surfaces of the two sections 6 and 7 and then immobilized on the top surface of the third section 10.

The resulting microcantilever deflection, z, from binding the analyte to the receptor can be described as the result of deflection of the ends 11 and 12 in one direction and deflection of the third section 10 in the same direction. Deflection of the third section 10 amplifies the deflection of the ends 11 and 12. Further, the influence of turbulence on deflections is reduced due to increased number of fixed ends. The increases in the deflection at the mid point 15 of the third section 10 results in decreasing the minimum detectable analyte concentration. This deflection at the midpoint of the microcantilever is expected to be:

$$Z = \frac{3.75 l^2 (1-\upsilon)}{Et^2} \Delta\sigma$$

wherein
l is the effective length of the microcantilever,
ν is Poisson's ratio,
E in Young's modulus,
Δσ is differential surface stress, and
t is the microcantilever thickness.

The C-shaped microcantilevers of the present invention have an effective stiffness that is larger than prior art microcantilevers such as the one shown in FIG. 1, and therefore, the C-shaped microcantilevers of the present invention will have turbulence effects that are lower than prior art microcantilevers. Table 3 compares the deflections of the microcantilevers of the present invention with prior art microcantilevers (ordinary).

TABLE 3

Summary of the performance of different microcantilevers

| z | Ordinary | C-shaped | Alternative E-shaped | L-shaped | Slit |
|---|---|---|---|---|---|
| Maximum $z_s$ | $z_o$ M/C length = L | 1.25 $z_o$ section length = L | ≈2.0 $z_o$ Intermediate section length = L | $z_o$ Total length = L | $\Delta z_s < z_o$ Slit length = L |
| $z_t$ | $z_{to}$ | 1.25 $z_{to}$ | ≈2.0 $z_{to}$ | 1.0 $z_{to}$ | $\Delta z_t < z_{to}$ |
| $z_d$ | $z_{do}$ | $<z_{do}$ at low ω | $<z_{do}$ at low ω | $<z_{do}$ | ≈0 |

* The length of the intermediate section is assumed to extend to the fixed end.

B. E-Shaped Microcantilever

Figure 11B:
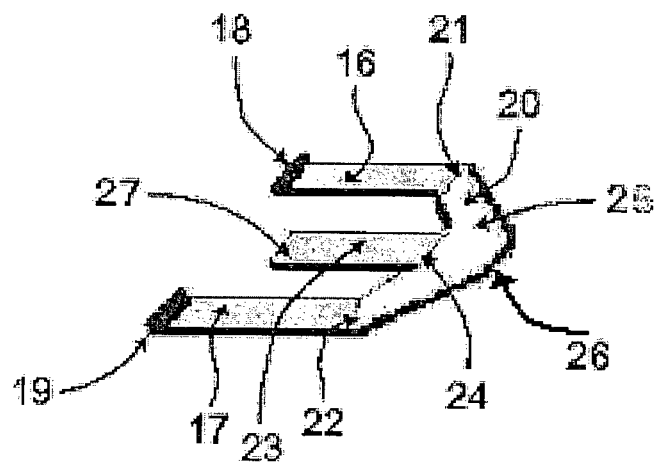
FIG. 11B is an E-shaped microcantilever wherein the third section lacks immobilized receptors.

FIG. 11B shows an E-shaped microcantilever of the present invention. E-shaped microcantilevers comprise two outer sections 16 and 17 that are attached to a support at ends 18 and 19, a third section 20 that is attached to the two outer sections 16 and 17 at ends 21 and 22, and an intermediate section 23 that is attached to the third section 20 at point 24 in between the two outer sections 16 and 17. The intermediate section 23 may act as a balance against flow turbulence. The sections may be synthesized as one structure or synthesized as three separate structures that are then connected together. Each section has a top surface 25 and a bottom surface 26. When used in an assay for detecting, measuring, or analyzing an analyte, a receptor R for the analyte may be immobilized on the top surfaces of the two outer sections 16 and 17 and on the bottom surface of the third section 20. Alternatively, the receptor R may be immobilized on the bottom surfaces of the two outer sections 16 and 17 and on the top surface of the third section 20. In another embodiment, no receptor R is immobilized to the third section 20. In any one of the embodiments, the receptor R may be immobilized on the top surface, the bottom surface, or both.

Figure 11C:
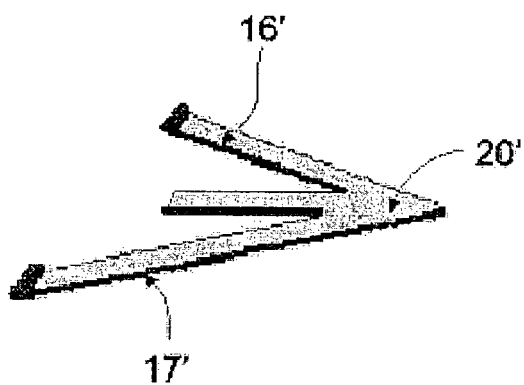
FIG. 11C is an E-shaped microcantilever wherein the first section and the second section form the third section.

FIG. 11C shows an alternative E-shape microcantilever of the present invention wherein the two outer sections 16' and 17' join to form the third section 20'.

The E-shaped microcantilever provides an increased number of fixed ends which results in an increase in the effective spring constant of the microcantilever. Since the influence of turbulence is inversely proportional to the effective spring constant, turbulence effects are reduced. The E-shaped microcantilever also provides nose deflections that are higher than those obtained with prior art microcantilevers due to increases in effective exterior mass loading especially where receptor coated nanostructures such as nanobeads and nanotubes are used. Moreover, where the deflection of the free end 27 of the intermediate section 23 is considered, deflections may be doubled if the receptor R on the intermediate section 23 is immobilized on an opposite surface to those of the two outer sections 16 and 17. Thus, both influences of turbulence on deflection measurements and the minimum detectable analyte concentration are reduced.

C. Tapered and Triangular Microcantilevers

Figure 11D:
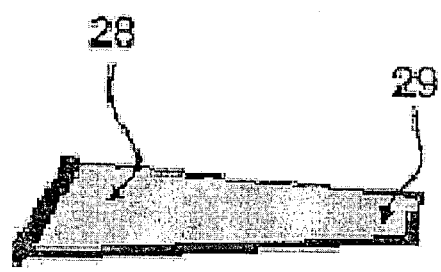
FIG. 11D is a tapered microcantilever.

FIG. 11D shows a microcantilever of the present invention has a tapered shape that increases its effective spring constant. As shown in FIG. 11D, the end 28 attached to the support is wider than the free end 29. The tapered microcantilever has tip deflections slightly greater than those for prior art microcantilevers having the same length due to the fact that increases in fixed area tend to reduce lateral motions, thereby resulting in a decrease on the effects of Poisson's ratio.

Figure 11E:
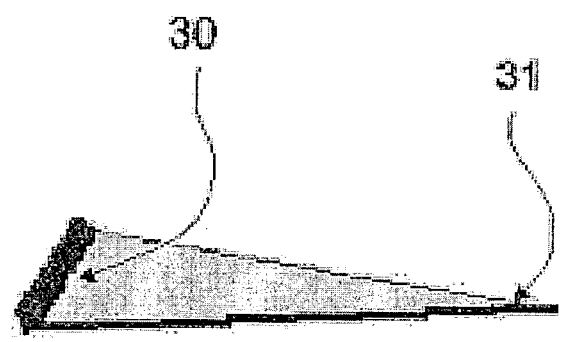
FIG. 11E is a triangular microcantilever.

Likewise, triangular microcantilevers of the present invention as shown in FIG. 11E will have higher spring constants than prior art microcantilevers so long as the fixed length is greater than 1.5 times the width of the prior art microcantilever. As shown in FIG. 11E, the end 30 attached to the support is wider than the free end 31 which comes to a point. There is a smaller area subject to drag for both the tapered and triangular microcantilevers. Thus, the area affected by flow turbulence is smaller.

D. L-Shaped Microcantilevers

Figure 11F:
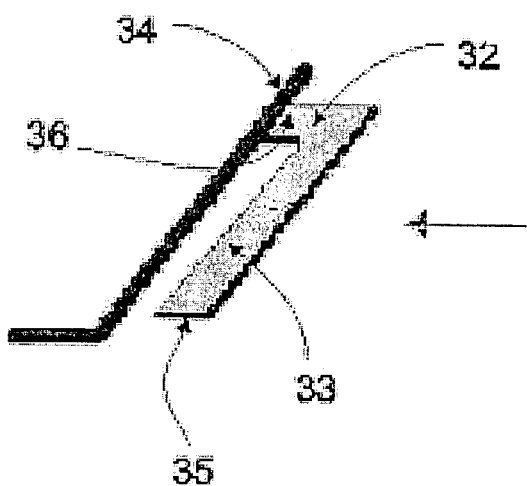
FIG. 11F is an L-shaped microcantilever wherein the direction of the flow of a fluid sample is transverse to length of the second section.
Figure 11G:
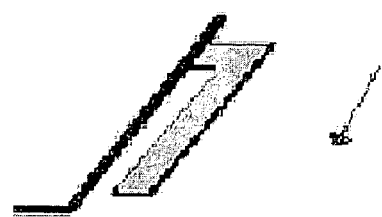
FIG. 11G is an L-shaped microcantilever wherein the direction of the flow of a fluid sample is parallel to length of the second section.

FIGS. 11F and 11G show L-shaped microcantilevers of the present invention which comprise a first section 32 and a second section 33, wherein the first section 32 has an end 34 that is attached to a solid support. When used in an assay for detecting, measuring, or analyzing an analyte, a receptor for the analyte R may be immobilized on the top surface or on the bottom surface of the microcantilever.

The L-shaped microcantilevers of the present invention are subjected to flow turbulences that are lower than prior art microcantilevers, thereby resulting in a decrease in the noise in the deflection measurements at the free end 35 of the second section 33 as turbulence fluctuations decrease near the solid support boundary 36. Accordingly, the length of the second section 33 can be longer than prior art microcantilevers. Thus, the L-shaped microcantilevers are more sensitive than prior art microcantilevers.

E. Double Microcantilever

Figure 11H:
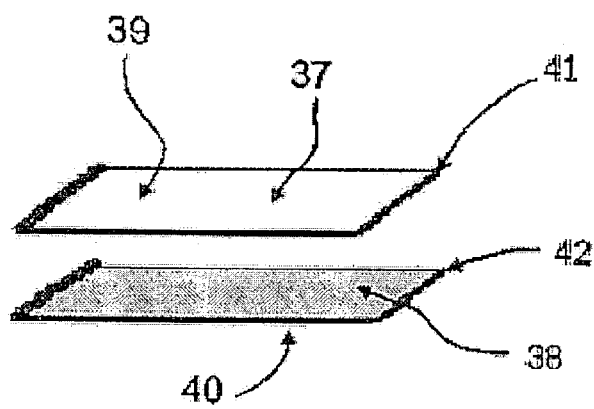
FIG. 11H is a double microcantilever.

FIG. 11H shows a double microcantilever of the present invention comprising one section 37 and a second section 38 separated by a distance ($z_{ref}$). When used in an assay for detecting, measuring, or analyzing an analyte, a receptor for the analyte R may be immobilized on the outer surfaces 39 and 40 of each section 37 and 38. Measuring the distance between the ends 41 and 42 of the sections provide increased accuracy over the prior art microcantilevers. Further, turbulence effects are reduced because the volume between the two sections 37 and 38 is almost inactive, thereby reducing the number of flow eddies. It should be noted that the reduced turbulence effects will still exist where the sections 37 and 38 have different immobilized receptors R. It should be noted that the double microcantilevers of the present invention may comprise a variety of shapes. For example, the two sections of a double microcantilever of the present invention may be C-shaped, E-shaped, tapered, triangular, or L-shaped.

For assays for a single analyte, the measured distance is given by $$z = \frac{6l^2(1-\nu)}{Et^2}\Delta\sigma + z_{ref}$$

wherein
l is the effective length of the microcantilever,
ν is Poisson's ratio,
E in Young's modulus,
Δσ is differential surface stress, and
t is the microcantilever thickness.

F. Slit Microcantilever

Figure 11I:
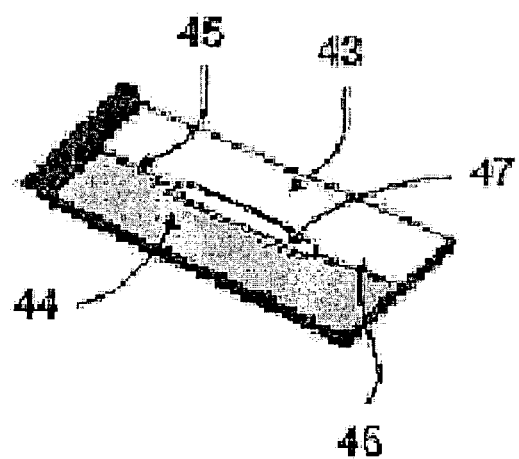
FIG. 11I is a microcantilever with a long slit.

FIG. 11I shows a slit microcantilever of the present invention which comprises two sections 43 and 44 attached to each other at points 45 and 46, and a slit 47. Each section has an upper surface and a bottom surface. When used in an assay for detecting, measuring, or analyzing an analyte, a receptor for the analyte R may be immobilized on upper surface of one section and on the bottom surface of the other section. When the analyte binds with the receptor R, no net deflections are expected. However, the slit 47 widens as sections try to deflect in opposite directions and the concentration of the analyte can be related to the width of the slit 47 which can be related to the number of photons from a laser source that passes through the slit 47. With this slit microcantilever, turbulence effect is greatly reduced because flow instabilities influence only deflections which are insignificant in the slit microcantilever.

Therefore, the present invention provides microcantilevers having different structural shapes. As provided herein, the microcantilevers of the present invention include C-shaped microcantilevers, E-shaped microcantilevers, tapered microcantilevers, triangular microcantilevers, L-shaped microcantilevers, double microcantilevers, and slit microcantilevers. The microcantilevers of the present invention may be used in a variety of methods and devices for assaying at least one analyte in a fluid sample.

The amount of bending of the microcantilevers of the present invention may be detected by several methods and systems known in the art. For example, the bending of the microcantilevers of the present invention may be detected by optical detection, capacitive detection, tunneling detection, and interferometric detection. See e.g. Bauer, P., et al. (1995) Ultramicroscopy 61(1-4):127-130; Brugger, J., et al. (1992) J. Micromechanics & Microengineering 2(3):218-220; Dragoman, D., et al. (2001) Applied Physics Letters 79(5): 581-583; Berger, R., et al. (1997) Science 276:2021-2024; Berger, R., et al. (1997) Microelectronic Engineering 35:373-379; Friz, J. et al. (2000) Science 288:316-318; Thaysen, J., et al. (1999) Proceedings of Transducers 99:1852-1855; and U.S. Pat. Nos. 6,203,983, 6,096,559, 5,972,617, 5,763,768, 5,719,324, 5,658,732, 5,445,008, and 5,345,815, which are herein incorporated by reference.

Nevertheless, these detection methods and systems require external devices for deflection measurements, such as lasers, optical fibers, and capacitors, which require periodic alignment and calibration.

Piezoresistive Microcantilevers

The problems of turbulence, drift, and noise associated with microcantilevers may also be alleviated by the use of piezoresistive microcantilevers having large piezoresistive effects. Therefore, in addition to microcantilevers having novel structural shapes, the present invention also provides piezoresistive microcantilevers with large piezoresistive effects.

Alcohol detection in gases has been performed on a polymer coated microcantilever. See Jensenius, H., et al. (2000) Applied Physics Letters 76(18):2615-2617. The detection of alkanethiol monolayer formation on gold coated microcantilevers in gases have indicated the change in the surface stress as a function of ethanol concentration in water by using commercially available piezoresistive microcantilevers. See Hansen, A. G., et al. (2001) Probe Microscope 2:139-149 and Boisen et al. (2000) Ultramicroscopy 82:11-16, which are herein incorporated by reference.

The resonance frequency of a microcantilever is very sensitive to the properties of the microcantilever surface. Changes in the surface properties of the microcantilever through binding or complexing of analytes to receptor molecules will directly influence the microcantilever resonance frequency by changing the overall microcantilever mass and the thickness of the binding layer. See Lu, P., et al. (2001) Mater. Phys. Mench. 4:51-55, which is herein incorporated by reference.

The fractional change in resistance ($\Delta R/R$) of a piezoresistive microcantilever may be described by the following Equation (27):

$$\frac{\Delta R}{R} = \beta \frac{3\pi_L(1-\nu)}{t_m}(\sigma_1 - \sigma_2) \quad (27)$$

wherein $\pi_L$ is the piezoresistive coefficient of Silicon along the <110> axis, $\sigma_1$ is the longitudinal stress, $\sigma_2$ is the transverse stress, $t_m$ is the thickness of the microcantilever, and $\beta$ is a factor that adjusts for the thickness of the piezoresistor.

See Harley and Kenny (1999) Applied Physica Letters 75(2):289-291, which is herein incorporated by reference.

From the above expression, the $\Delta R/R$ ratio is proportional to the stress difference, $\sigma_1-\sigma_2$. The stress difference distribution depends on the geometric factors of the layers and the chemo-mechanical forces between the ligands, receptors, and the hybridization layers. Therefore, the deflection signal can be increased by maximizing the stress difference, $\sigma_1-\sigma_2$, by changing the geometric factors of the layers. See Kassegne, S. et al. (2002) Proceedings of the SPIE Conference on Smart Structures and Materials, San Diego, Calif., which is herein incorporated by reference. In addition, the method of stress concentration regions (SCRs) can be employed (as discontinuity holes) to further increase the stress difference, thereby giving rise to an increased sensitivity in detection of a given analyte. A double microcantilever of the present invention may be used to increase the differential stress ($\sigma_1-\sigma_2$).

Modeling and simulations for the piezoresistive microcantilever of the present invention were conducted using CFDRC™ from the CFD Research Corporation, Sunnyvale, Calif.). The microcantilever was assumed to be 40 μm in width and 150 μm in length and the length of the piezoresistive layer was taken to be 100 μm. For the properties of the piezoresistive layer, were the parameters of the PZT-8 system from Morgan Matroc, Inc. The following matrices represent the piezoresistive parameters of the PZT-8 system:

A. The 3-D dielectric matrix:

$$[\varepsilon] = \begin{bmatrix} 8003 & 0 & 0 \\ 0 & 8003 & 0 \\ 0 & 0 & 2252 \end{bmatrix} \times 10^{-9} \text{Farads/meter}$$

B. The 3-D piezoelectric matrix:

$$[D] = \begin{bmatrix} 0 & 0 & -388 \\ 0 & 0 & -388 \\ 0 & 0 & 1391 \\ 0 & 0 & 0 \\ 0 & 1034 & 0 \\ 1034 & 0 & 0 \end{bmatrix} C/m^2$$

Figure 12:
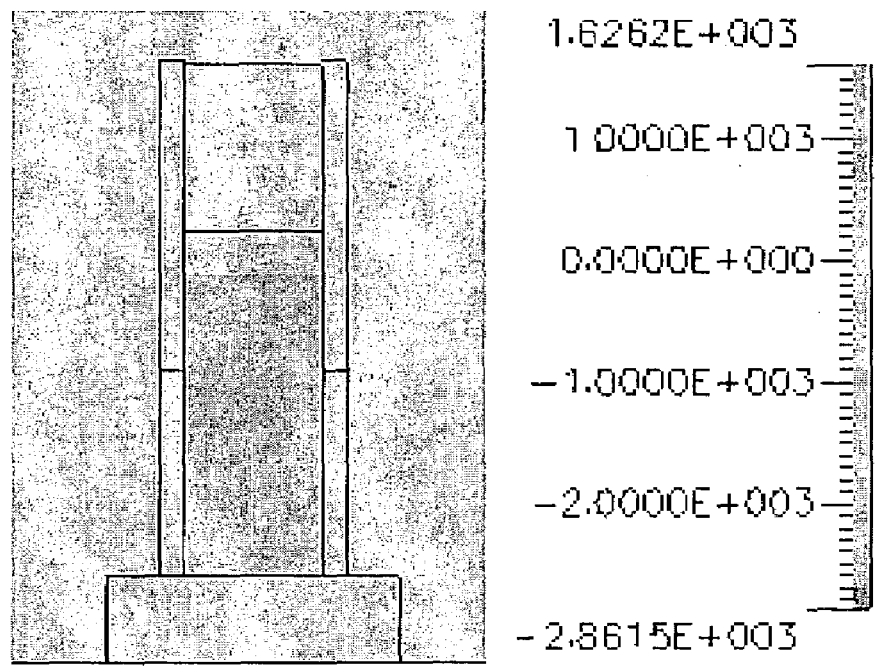
FIG. 12 shows the stress difference $(\sigma_1-\sigma_2)$ distribution in a piezoresistive microcantilever.
Figure 14:
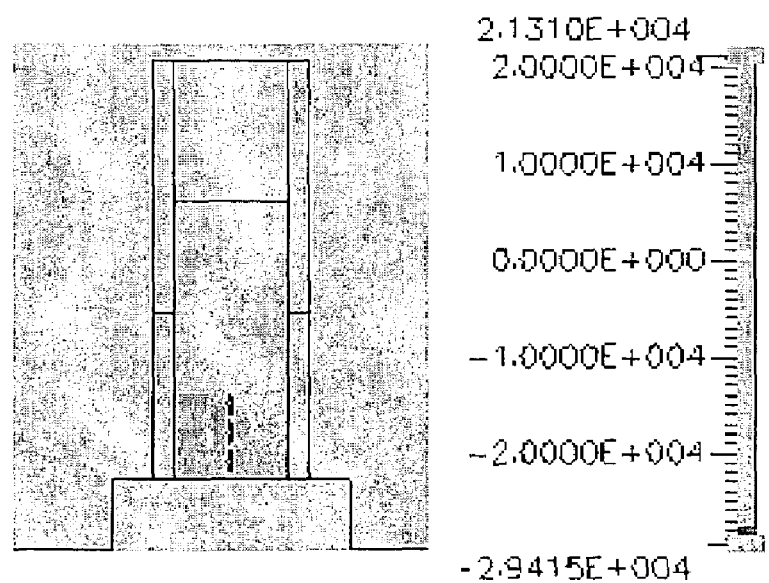
FIG. 14 shows the stress difference $(\sigma_1-\sigma_2)$ distribution in a piezoresistive microcantilever with SCRs.
Figure 13:
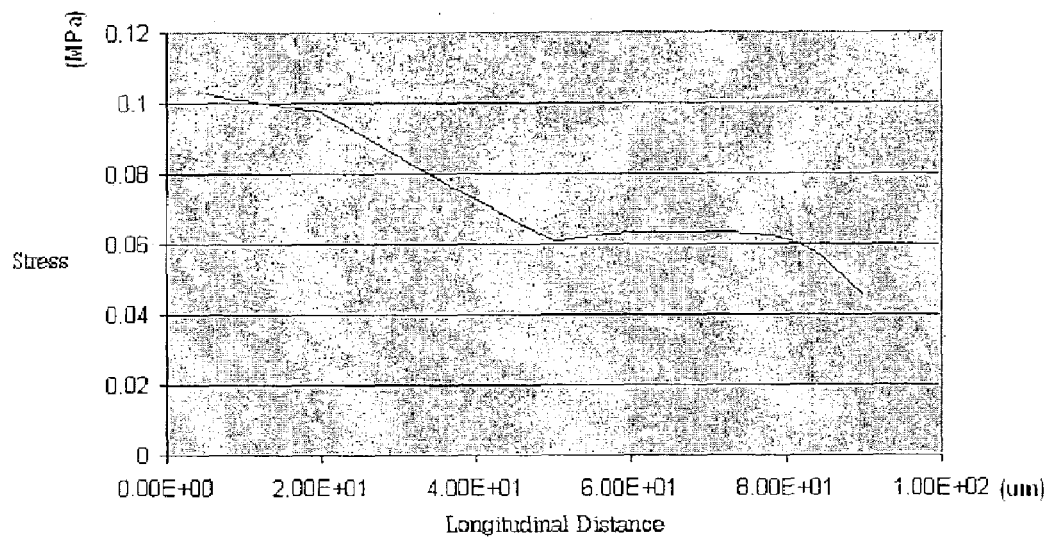
FIG. 13 shows the integrated stress difference along the longitudinal axis of a microcantilever.
Figure 15:
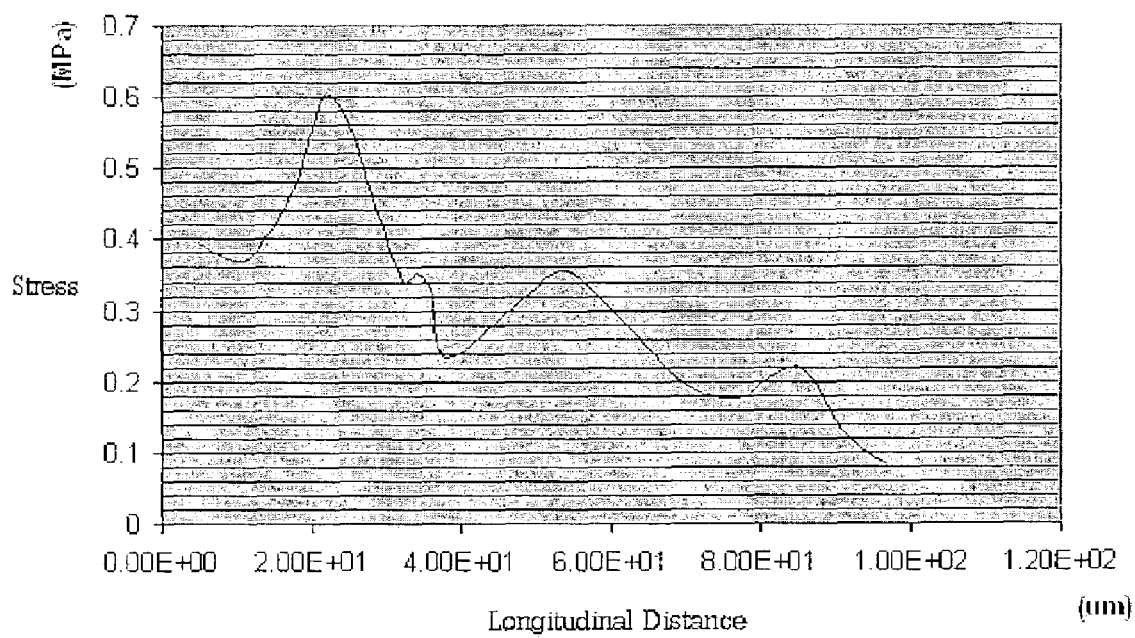
FIG. 15 shows the integrated stress difference $(\sigma_1-\sigma_2)$ along the longitudinal axis of microcantilevers with SCRs.
Figure 16:
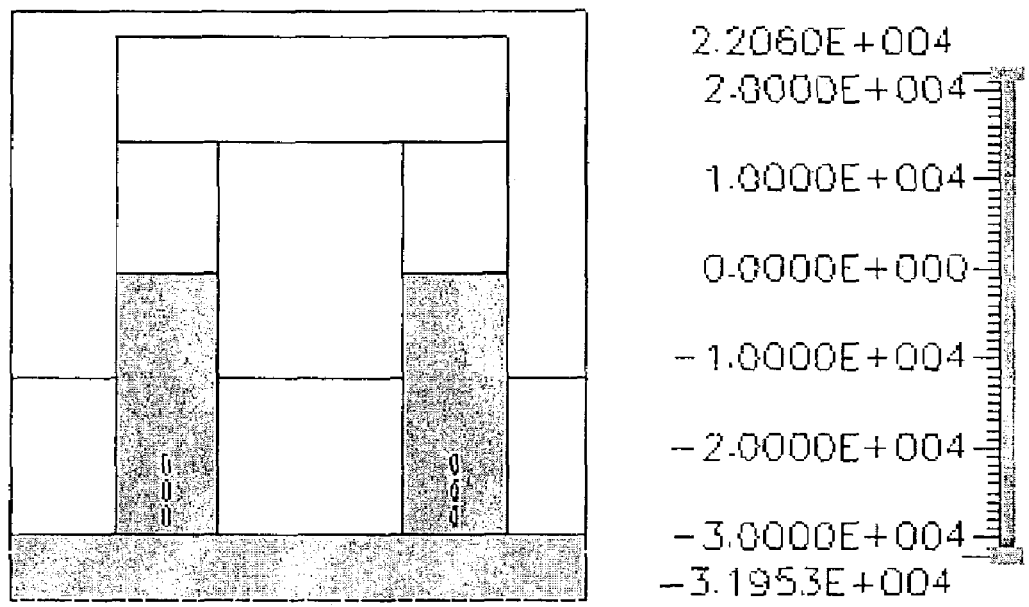
FIG. 16 shows the stress difference $(\sigma_1-\sigma_2)$ distribution for a C-Shaped piezoresistive microcantilever.
Figure 17:
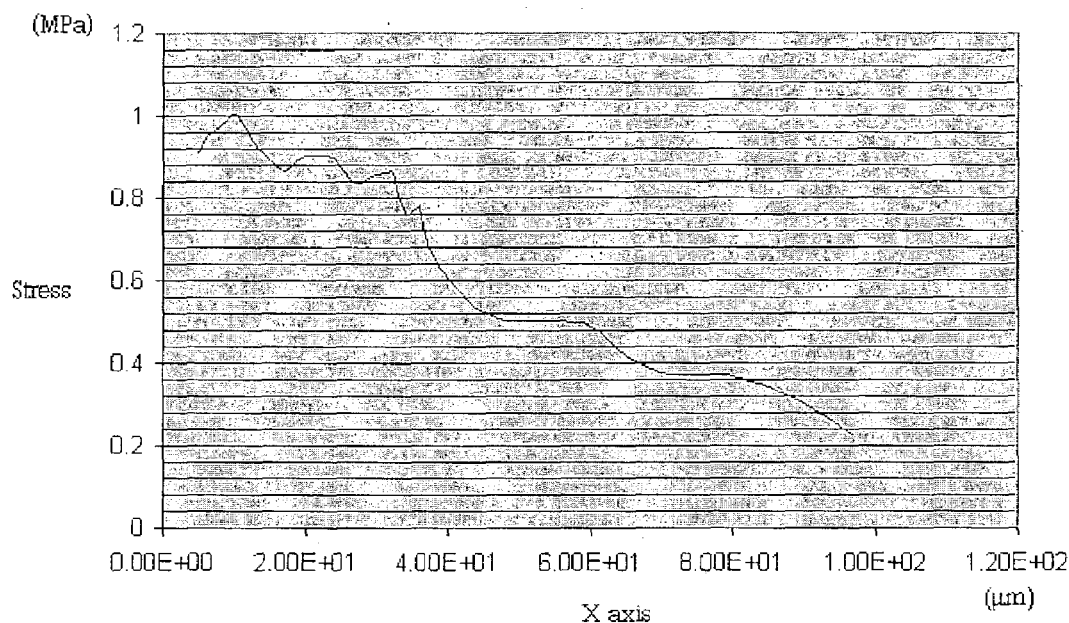
FIG. 17 shows the integrated stress difference $(\sigma_1-\sigma_2)$ along the longitudinal axis for a C-Shaped piezoresistive microcantilever.

Three simulations were conducted with the same conditions of analyte concentration and the same analyte capturing area. For the C-Shaped microcantilever of the present invention, the capture area was designed to be the whole area of the third section. For a piezoresistive microcantilever having the ordinary microcantilever shape as shown in FIG. 12, the quantity of stress difference ($\sigma_1-\sigma_2$) is maximized near the microcantilever support area as expected. FIG. 13 shows the integrated value of ($\sigma_1-\sigma_2$) over the length of the microcantilever where over the capture area, the value of ($\sigma_1-\sigma_2$) is constant about 0.06 MPa. Towards the microcantilever support area, the value of ($\sigma_1-\sigma_2$) increases to about 0.1 MPa. For a single piezoresistive microcantilever with stress concentration regions (SCRs) as shown in FIG. 14, the stress difference ($\sigma_1-\sigma_2$) further increases near the support area to a maximum value of 0.6 MPa over a plateau that is 30 microns in length as shown in FIG. 15. Therefore, around or near the support area is the preferred region for placing a piezoelectric layer to collect large displacement signals. For a C-shaped microcantilever shape having a piezoresistive layer with SCRs in FIG. 16, the maximum value of the stress difference increases to nearly 1 MPa, and the length of the "flat roof" area with large ($\sigma_1-\sigma_2$) increases to 60 μm, which means that the effective signal collecting area is increased as shown in FIG. 17.

It should be noted that Equation (2) may be reduced to Equation (28) as follows:

$$\frac{\Delta R}{R} = \Pi[(\Delta \sigma_1)_0 - (\Delta \sigma_2)_0]\left[1 - e^{-\overline{k}_f N_r(1+\alpha\omega)\left((C_\infty)_o t + \frac{\beta_c}{\omega}(\cos(\omega t)-1)\right)}\right] \quad (28)$$

wherein $$\Pi = \beta \frac{3\pi_L(1-\nu)}{t}$$

is the piezoresistor coefficient,
$(\Delta\sigma_1)_0 = \Delta G_1 N_o A_m^{-1} A^{-1}$, and
$(\Delta\sigma_2)_0 = \Delta G_2 N_o A_m^{-1} A^{-1}$.

Since the effective binding rate can be linearly correlated to the analyte rolling velocity and the translational velocity, such that:

$$\bar{k}_f = \bar{k}_{fo} - b|u| \tag{13}$$

where $\bar{k}_{fo}$ and b are constants greater than zero. Therefore, Equation (28) can be further reduced to Equation (29):

If the effect of turbulence is ignored, i.e. when the flow is fully developed, Equation (29) may be simplified to Equation (30):

$$\frac{\Delta R}{R} = \Pi[(\Delta\sigma_1)_0 - (\Delta\sigma_2)_0]\left[1 - e^{-(\bar{k}_{fo} - b|u|)N_r C_\infty t}\right] \tag{30}$$

Figure 18:
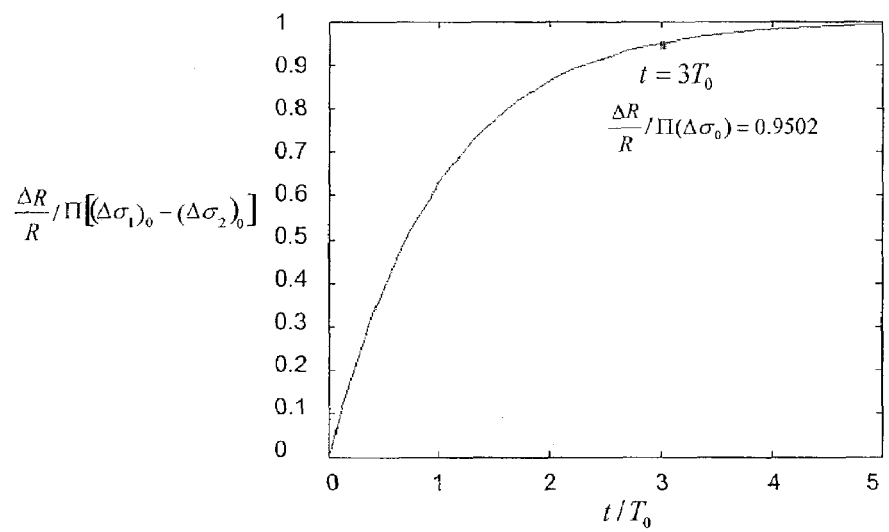
FIG. 18 is a graph showing resistance changes versus time due to analyte-receptor binding.

FIG. 18 is a graph showing resistance changes versus time due to analyte-receptor binding. From FIG. 18, $T_0 = 1/(\bar{k}_{fo} - b|u|)N_r C_\infty$, the change of resistance almost reaches the maximum when $t = 3T_0$.

The above-referenced model shown in FIG. 2 was used. However, since the ratio ($\Delta R/R$) is proportional to the stress difference ($\Delta\sigma$), any geometrical enhancements to maximize the stress difference will result in increasing sensitivity of detection. Therefore, for the finite element simulations, elliptical holes located in the piezoresistive area of a microcantilever were used to maximize the integrated stress difference. The microcantilever used was 30 μm wide and 120 μm long with a thickness of 1 m. The piezoresistive layer had a depth of 0.1 μm. The length of the piezoresistive layer was 80 μm, which covered the most area near the solid support. The capture area was located at the top surface of the microcantilever.

Figure 19:
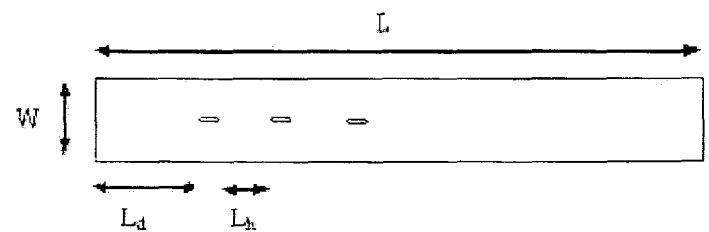
FIG. 19 shows the top view of a piezoresistive microcantilever with elliptical holes.

As shown in FIG. 19, three elliptical holes were located on the microcantilever such that the distance between the holes are given by $L_h$. $L_d$ is the distance between the first hole and the solid support to which the microcantilever is attached. W and L are the width and the length of the microcantilever, respectively. For the simulation results shown in FIG. 20, t=0.1 μm, L=120 μm, W=30 μm, $L_d$=15 μm and $L_h$=12 μm. In addition, $R_t$=2 μm is the transverse axis length, $R_1$=8 μm is length of the longitudinal axis and the hole axis hole ratio ($R_1$:$R_t$).

Figure 20A:
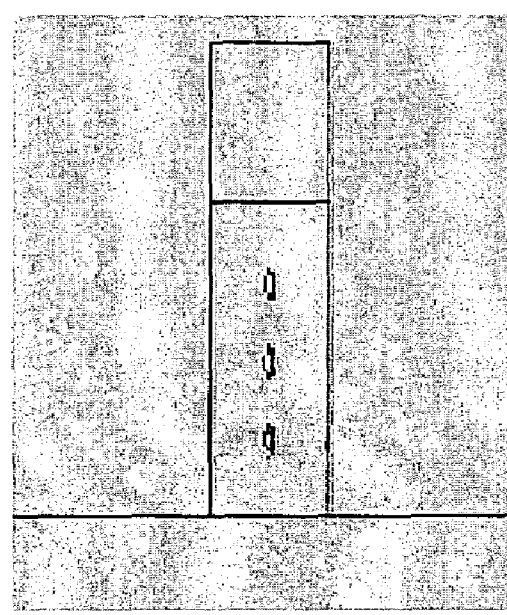
FIG. 20A shows differential stress distribution for an SCR microcantilever.
Figure 20B:
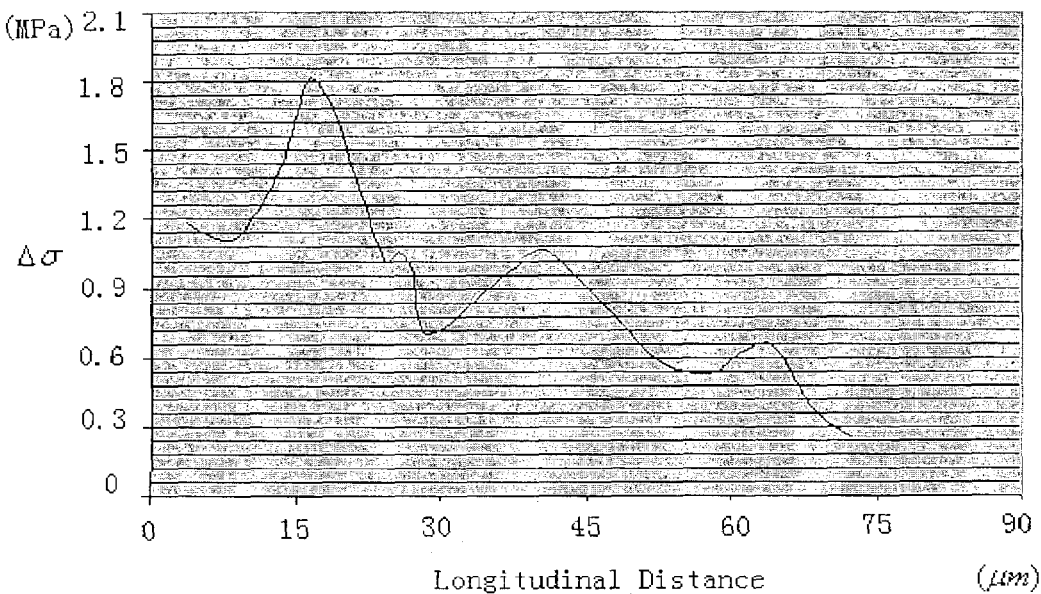
FIG. 20B shows integrated differential stress along the longitudinal axis of an SCR microcantilever
Figure 20C:
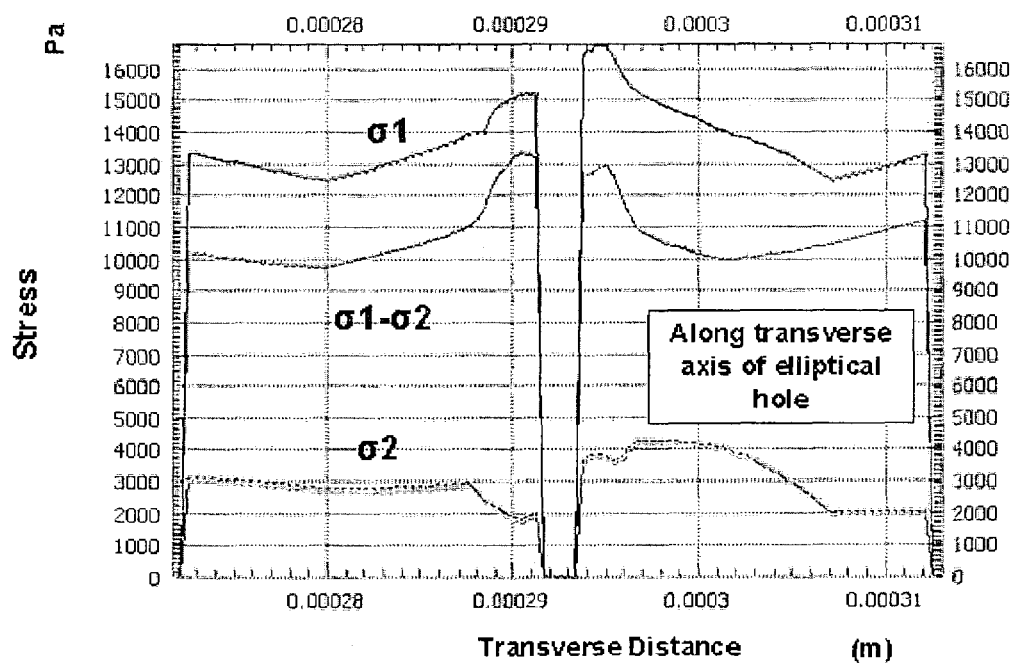
Figure 20D:
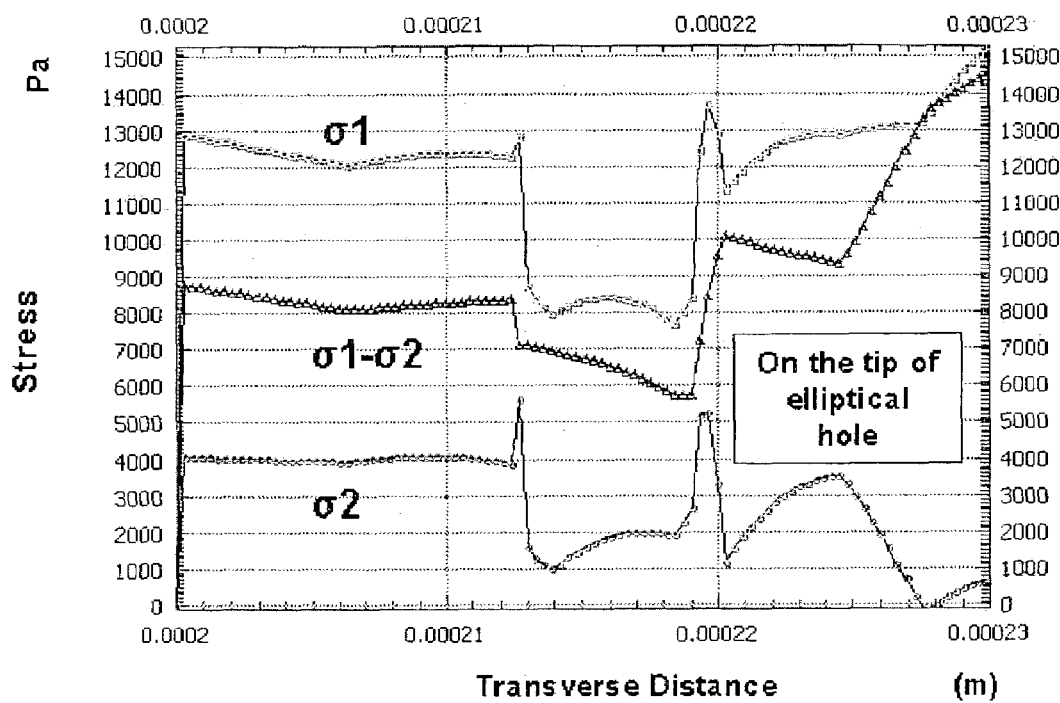

As shown in FIG. 20A, the value of the stress difference is concentrated around the holes, and is maximized around the first hole which is closest to the supporting post. As shown in FIG. 20B, three peaks in the integrated stress difference were observed near the holes. Between the three peaks, two local minimum points or bottoms were observed because the long axis of elliptical holes is along the longitudinal axis of microcantilever, the effect of discontinuity causes the stress contours to change. A sharp increase in the longitudinal stress, $\sigma_1$, was obtained on the cross section of the hole position, and no obvious change for the transverse stress, $\sigma_2$, was observed as shown in FIG. 20C. As shown in FIG. 20D, the effect of SCRs decreases sharply as the distance from the hole position increases.

Figure 21:
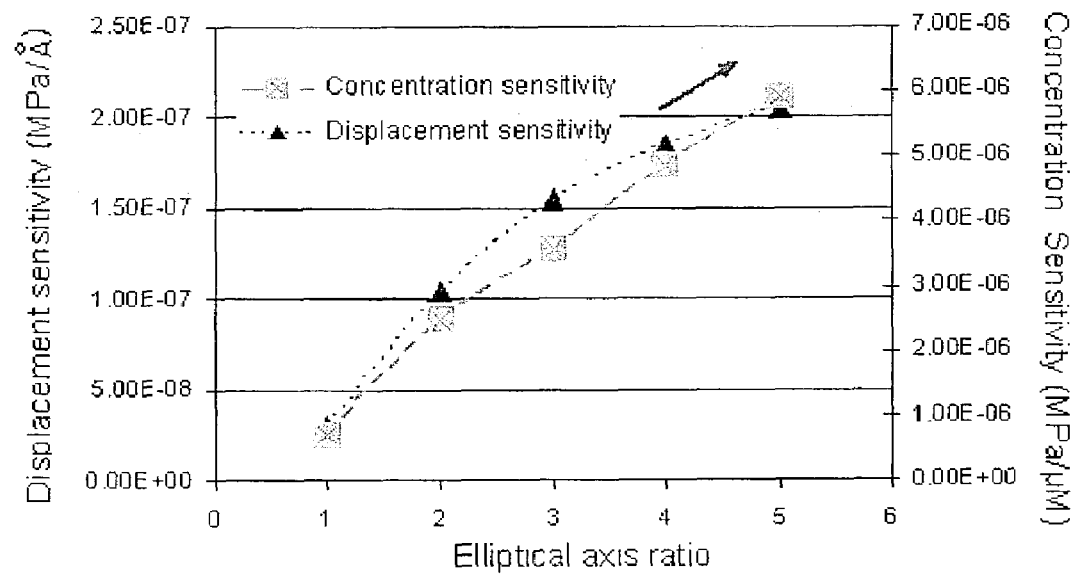
FIG. 21 shows displacement sensitivity, analyte concentration sensitivity, and resonance frequency change for a rectangular microcantilever with different SCR axis ratio elliptical holes.

Different axis ratios of elliptical holes have been utilized for the simulations, which resulted in different effects on the microcantilever sensitivity as shown in Table 4 and FIG. 21, where $C_\infty$ is initial surface analyte concentration, D is the displacement of the microcantilever, k is the spring constant of the microcantilever and F is the resonance frequency of the microcantilever.

TABLE 4

Displacement sensitivity, analyte concentration sensitivity, and resonance frequency change for rectangular microcantilever with different SCR axis ratio elliptical holes

|  | L = 120 μm<br>W = 30 μm<br>(No CSR) | $R_t$ = 4 μm<br>$R_t$ = 2 μm<br>t = 0.1 μm<br>$L_d$ = 15 μm<br>$L_h$ = 20 μm | $R_t$ = 6 μm<br>$R_t$ = 2 μm<br>t = 0.1 μm<br>$L_d$ = 15 μm<br>$L_h$ = 20 μm | $R_t$ = 8 μm<br>$R_t$ = 2 μm<br>t = 0.1 μm<br>$L_d$ = 15 μm<br>$L_h$ = 20 μm | $R_t$ = 10 μm<br>$R_t$ = 2 μm<br>t = 0.1 μm<br>$L_d$ = 15 μm<br>$L_h$ = 20 μm |
|---|---|---|---|---|---|
| $\frac{\Delta R}{R}/(D\Pi)$ (MPa/Å) | 2.99 × 10$^{-8}$ | 1.05 × 10$^{-7}$ | 1.54 × 10$^{-7}$ | 1.85 × 10$^{-7}$ | 2.05 × 10$^{-7}$ |
| $\frac{\Delta R}{R}/(C_0\Pi)$ (MPa/μM) | 7.16 × 10$^{-7}$ | 2.50 × 10$^{-6}$ | 3.58 × 10$^{-6}$ | 4.84 × 10$^{-6}$ | 5.92 × 10$^{-6}$ |
| K(N/m) | 1.04 × 10$^{-1}$ | 9.24 × 10$^{-2}$ | 8.60 × 10$^{-2}$ | 7.64 × 10$^{-2}$ | 6.75 × 10$^{-2}$ |
| F(kHz) | 15.78 | 15.23 | 14.91 | 14.23 | 13.52 |

The simulations indicate that high axis ratio holes increase the stress difference, i.e. increase the magnitude of the "peaks" in the integrated stress difference, which results in increased signal sensitivity. Both the vertical displacement sensitivity and the analyte concentration sensitivity increase with the increasing of the axial ratio of the elliptical holes. Both the spring constant, k, and the resonance frequency, F, decrease with the increasing of the axis ratio.

Figure 22:
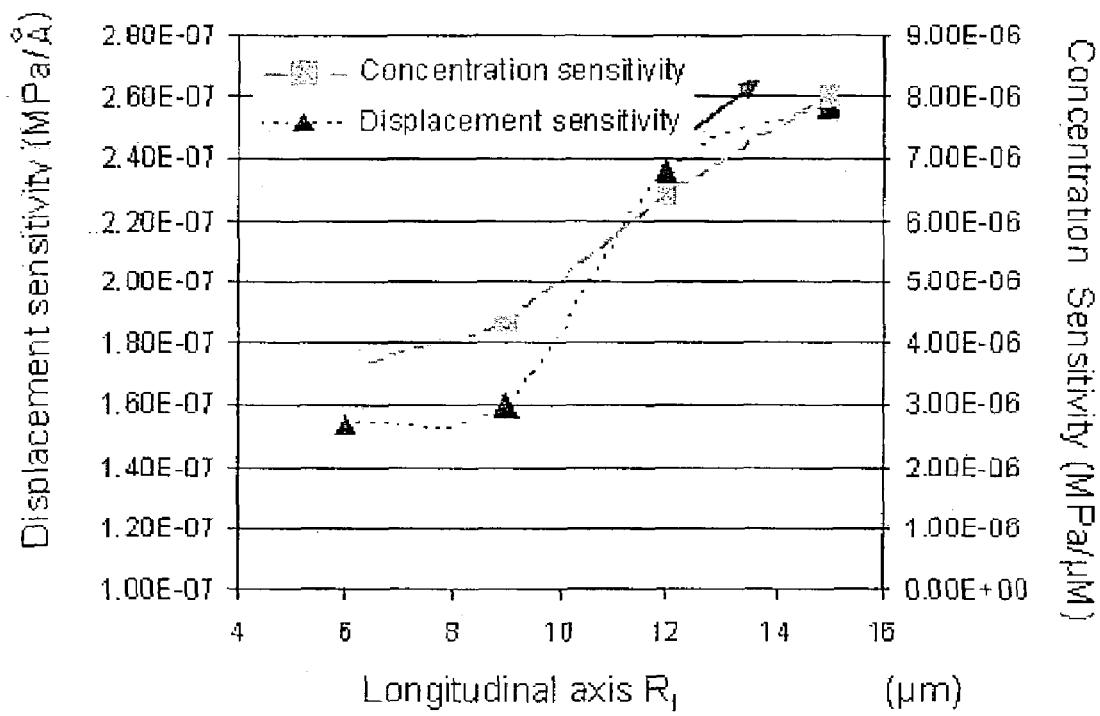
FIG. 22 shows the parameters for SCR different hole scale sizes.
Figure 23:
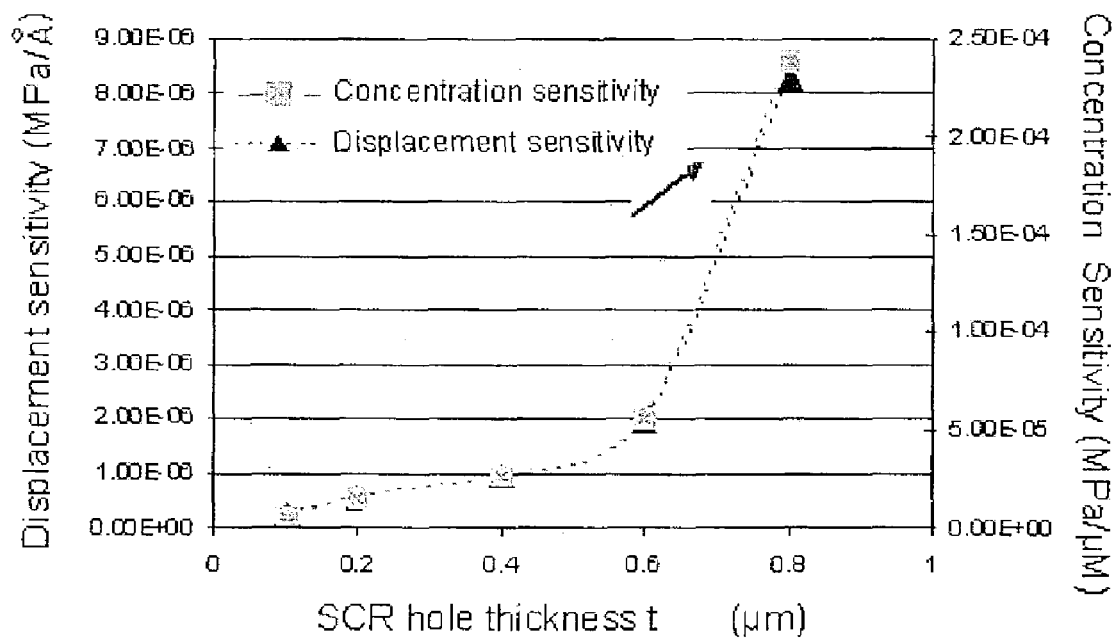
FIG. 23 shows the parameters for SCR thickness.

As shown in FIG. 22 and FIG. 23 changes in the size of the holes and changes in the thickness of the sections around the holes have effects on microcantilever sensitivities. Table 5 provides the parameters for SCR different hole scale sizes.

TABLE 5

Parameters for SCR different hole scale size

| | | | | |
|---|---|---|---|---|
| | $R_l = 6$ μm | $R_l = 9$ μm | $R_l = 12$ μm | $R_l = 15$ μm |
| | $R_t = 2$ μm | $R_t = 3$ μm | $R_t = 4$ μm | $R_t = 5$ μm |
| | $t = 0.1$ μm | $t = 0.1$ μm | $t = 0.1$ μm | $t = 0.1$ μm |
| | $L_d = 15$ μm | $L_d = 15$ μm | $L_d = 15$ μm | $L_d = 15$ μm |
| | $L_h = 20$ μm | $L_h = 20$ μm | $L_h = 20$ μm | $L_h = 20$ μm |
| $\frac{\Delta R}{R} / (D\Pi)$ (MPa/Å) | $1.54 \times 10^{-7}$ | $1.60 \times 10^{-7}$ | $2.36 \times 10^{-7}$ | $2.57 \times 10^{-7}$ |
| $\frac{\Delta R}{R} / (C_0\Pi)$ (MPa/μM) | $3.58 \times 10^{-6}$ | $4.28 \times 10^{-6}$ | $6.42 \times 10^{-6}$ | $8.02 \times 10^{-6}$ |
| K(N/m) | $8.60 \times 10^{-2}$ | $7.47 \times 10^{-2}$ | $7.35 \times 10^{-2}$ | $6.41 \times 10^{-2}$ |
| F(KHz) | 14.91 | 14.36 | 13.96 | 12.83 |

Table 6 provides the parameters for SCR thickness.

TABLE 6

Parameters for SCR thickness

| | | | | | |
|---|---|---|---|---|---|
| | $R_l = 12$ μm | $R_l = 12$ μm | $R_l = 12$ μm | $R_l = 12$ μm | $R_l = 12$ μm |
| | $R_t = 4$ μm | $R_t = 4$ μm | $R_t = 4$ μm | $R_t = 4$ μm | $R_t = 4$ μm |
| | $t = 0.1$ μm | $t = 0.2$ μm | $t = 0.4$ μm | $t = 0.6$ μm | $t = 0.8$ μm |
| | $L_d = 15$ μm | $L_d = 15$ μm | $L_d = 15$ μm | $L_d = 15$ μm | $L_d = 15$ μm |
| | $L_h = 20$ μm | $L_h = 20$ μm | $L_h = 20$ μm | $L_h = 20$ μm | $L_h = 20$ μm |
| $\frac{\Delta R}{R} / (D\Pi)$ (MPa/Å) | $2.36 \times 10^{-7}$ | $5.34 \times 10^{-7}$ | $9.55 \times 10^{-7}$ | $1.98 \times 10^{-6}$ | $8.27 \times 10^{-6}$ |
| $\frac{\Delta R}{R} / (C_0\Pi)$ (MPa/μM) | $6.42 \times 10^{-6}$ | $1.47 \times 10^{-5}$ | $2.68 \times 10^{-5}$ | $5.58 \times 10^{-5}$ | $2.38 \times 10^{-4}$ |
| KN/m | $7.35 \times 10^{-2}$ | $7.29 \times 10^{-2}$ | $7.13 \times 10^{-2}$ | $7.09 \times 10^{-2}$ | $6.94 \times 10^{-2}$ |
| F(KHz) | 13.96 | 13.78 | 13.35 | 13.23 | 13.12 |

With an increase in size or thickness, both the displacement and the analyte concentration sensitivities of the microcantilever increase, and the spring constant and resonance frequency of the microcantilever decrease. Overall, a large size hole, a large aspect ratio, and a large thickness of the elliptical hole dimensions increase the sensitivity in spite of the slightly decreasing spring constant.

Decreasing the distance, $L_d$, between the first hole and the solid support will increase both the displacement and the analyte concentration sensitivities. Table 7 provides the parameters for variable distances to the solid support.

TABLE 7

Parameters for variable distance to support

| Parameters | | | |
|---|---|---|---|
| | $R_l = 8$ μm | $R_l = 8$ μm | $R_l = 8$ μm |
| | $R_t = 2$ μm | $R_t = 2$ μm | $R_t = 2$ μm |
| | $t = 0.1$ μm | $t = 0.1$ μm | $t = 0.1$ μm |
| | $L_h = 20$ μm | $L_h = 20$ μm | $L_h = 20$ μm |
| | $L_d = 15$ μm | $L_d = 10$ μm | $L_d = 5$ μm |
| $\frac{\Delta R}{R} / (D\Pi)$ (MPa/Å) | $1.85 \times 10^{-7}$ | $2.13 \times 10^{-7}$ | $2.37 \times 10^{-7}$ |
| $\frac{\Delta R}{R} / (C_0\Pi)$ (MPa/μM) | $4.84 \times 10^{-6}$ | $6.48 \times 10^{-6}$ | $7.82 \times 10^{-5}$ |
| K(N/m) | $7.64 \times 10^{-2}$ | $6.57 \times 10^{-2}$ | $6.06 \times 10^{-2}$ |
| F(KHz) | 14.23 | 13.54 | 12.54 |

Figure 24:
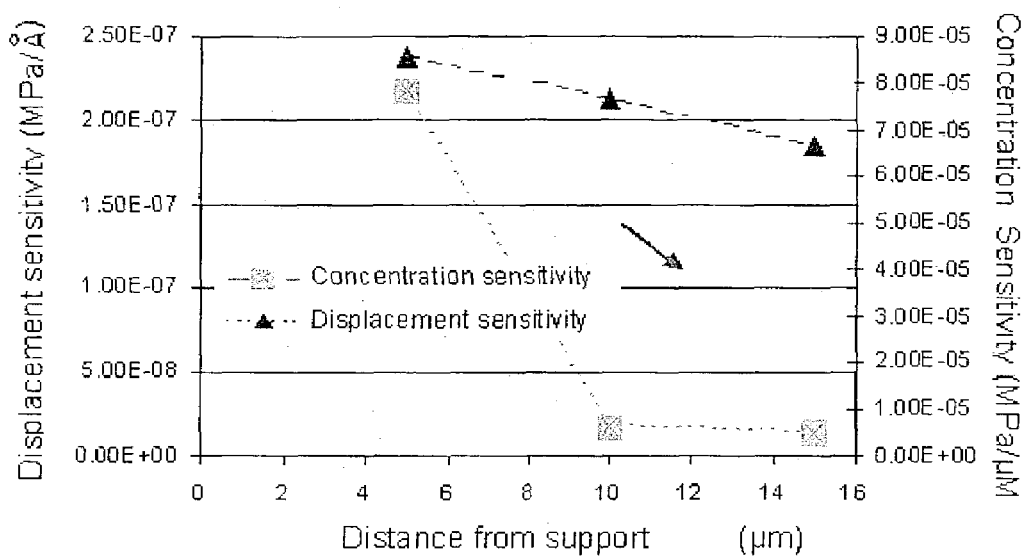
FIG. 24 shows the parameters for variable distance to the solid support.

In addition, the spring constant and resonance frequency of the microcantilever will decrease as provided in FIG. 24.

Figure 25:
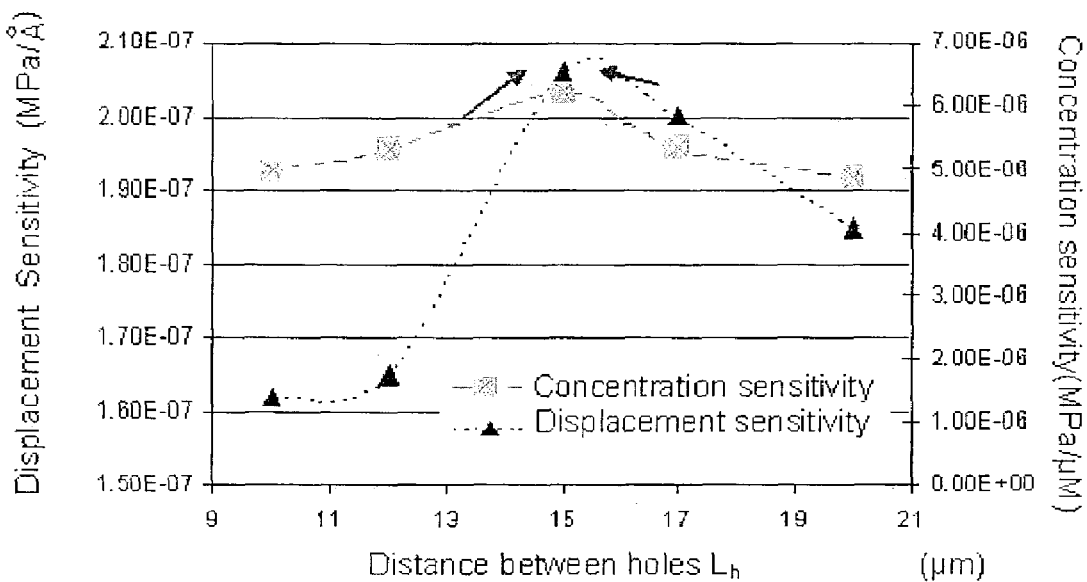
FIG. 25 shows the parameters for variable distance between holes $L_h$.

If the location of the second hole in the microcantilever is fixed and the distance between the holes, $L_h$, is shortened, both the displacement and the analyte concentration sensitivities will increase when $L_h$ is decreased from 20 μm to 15 μm as shown in FIG. 25. Table 8 provides the parameters for variable distances between the holes.

TABLE 8

Parameters for variable distance between holes $L_h$

| Parameters | $R_l = 8\ \mu m$<br>$R_t = 2\ \mu m$<br>$t = 0.1\ \mu m$<br>$L_h = 20\ \mu m$ | $R_l = 8\ \mu m$<br>$R_t = 2\ \mu m$<br>$t = 0.1\ \mu m$<br>$L_h = 17\ \mu m$ | $R_l = 8\ \mu m$<br>$R_t = 2\ \mu m$<br>$t = 0.1\ \mu m$<br>$L_h = 15\ \mu m$ | $R_l = 8\ \mu m$<br>$R_t = 2\ \mu m$<br>$t = 0.1\ \mu m$<br>$L_h = 12\ \mu m$ | $R_l = 8\ \mu m$<br>$R_t = 2\ \mu m$<br>$t = 0.1\ \mu m$<br>$L_h = 10\ \mu m$ |
|---|---|---|---|---|---|
| $\frac{\Delta R}{R} / (D\Pi)$ (MPa/Å) | $1.85 \times 10^{-7}$ | $2.00 \times 10^{-7}$ | $2.06 \times 10^{-7}$ | $1.65 \times 10^{-7}$ | $1.62 \times 10^{-7}$ |
| $\frac{\Delta R}{R} / (C_0\Pi)$ (MPa/μM) | $4.84 \times 10^{-6}$ | $5.34 \times 10^{-6}$ | $6.20 \times 10^{-6}$ | $5.32 \times 10^{-6}$ | $4.96 \times 10^{-6}$ |
| F(KHz) | 14.23 | 13.46 | 13.55 | 13.50 | 13.38 |

If $L_h$ is decreased further, both sensitivities will also start to decrease. Therefore, the optimum distance between the holes is two times the length of the long axis length.

Figure 26:
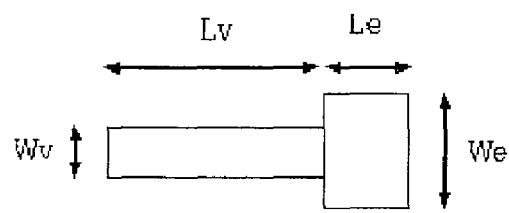
FIG. 26 shows the geometry parameters for variable cross section.

Simulations have indicated that variable width of the cross section of microcantilever geometry can be used to increase the sensitivity. FIG. 26 shows a microcantilever wherein $W_v$ is the width of the microcantilever near the support; $W_e$ is the width of the microcantilever at the end; $L_v$ is the length of microcantilever close to the support and $L_e$ is the length of microcantilever at the end. Table 9 provides the parameters of variable widths of the cross section.

Figure 27:
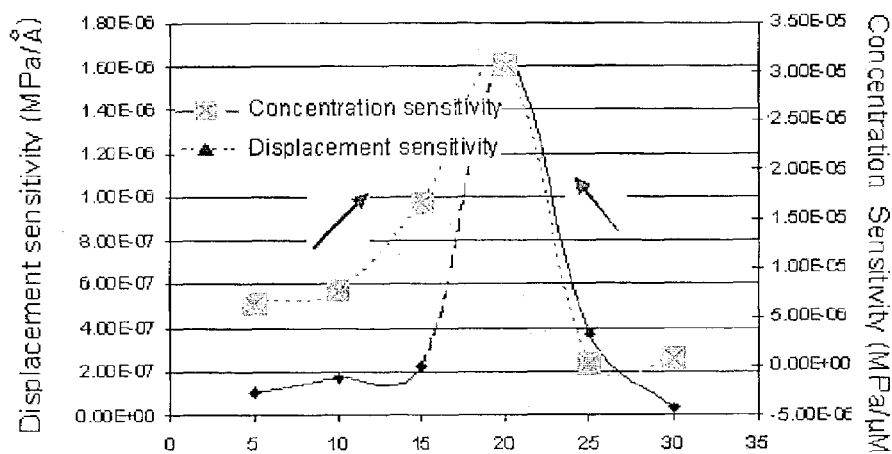
FIG. 27 shows the parameters of variable width of a microcantilever.

The displacement and the analyte concentration sensitivities increase when $W_v$ decreases from 30 μm to 20 μm as shown in FIG. 21. This is because the differential stress reaches the maximum around $W_v=20$ μm for the increasing extent of the SCR. When $W_v$ decreases further, the decrease in the microcantilever spring constant will dominate, and hence both the displacement and the analyte concentration sensitivities decrease. Since the ratio $L_v:L_e=3:2$, it is reasonable to find that the maximum sensitivity is obtained when $W_e:W_v=3:2$. The parameters for variable widths of the microcantilever are provided in FIG. 27.

In summary:

The differential stress ($\sigma_1-\sigma_2$) is concentrated in the area near the support post.

SCR (holes) can increase the magnitude of the differential stress ($\sigma_1-\sigma_2$). In the case of elliptical holes, a large axis ratio, large hole dimensions and deep hole thickness can increase both the displacement and analyte concentration sensitivities even though the microcantilever spring constant decreases.

For integrated differential stress ($\sigma_1-\sigma_2$), the peaks are obtained in positions around the holes.

The optimal distance between holes is taken as twice of the longitudinal axis of elliptical holes Moving holes closer to the support increases both the displacement and the analyte concentration sensitivities.

Decreasing cross section close to support will increase the displacement and analyte concentration sensitivities. The sensitivities first reach the maximum and then decrease. The optimum ratio is $L_v:L_e=W_e:W_v$ Based on the simulations above, an SCR modified C-shaped microcantilever was designed to increase the overall detection sensitivity. The geometrical parameters for SCR modified C-shaped microcantilevers are provided in Table 10.

TABLE 9

Parameters of variable width of microcantilever

| Parameters | $L_v = 80\ \mu m$<br>$L_e = 40\ \mu m$<br>$W_e = 30\ \mu m$<br>$W_v = 30\ \mu m$ | $L_v = 80\ \mu m$<br>$L_e = 40\ \mu m$<br>$W_e = 30\ \mu m$<br>$W_v = 25\ \mu m$ | $L_v = 80\ \mu m$<br>$L_e = 40\ \mu m$<br>$W_e = 30\ \mu m$<br>$W_v = 20\ \mu m$ | $L_v = 80\ \mu m$<br>$L_e = 40\ \mu m$<br>$W_e = 30\ \mu m$<br>$W_v = 15\ \mu m$ | $L_v = 80\ \mu m$<br>$L_e = 40\ \mu m$<br>$W_e = 30\ \mu m$<br>$W_v = 10\ \mu m$ | $L_v = 80\ \mu m$<br>$L_e = 40\ \mu m$<br>$W_e = 30\ \mu m$<br>$W_v = 5\ \mu m$ |
|---|---|---|---|---|---|---|
| $\frac{\Delta R}{R} / (D\Pi)$ (MPa/Å) | $2.99 \times 10^{-8}$ | $3.71 \times 10^{-7}$ | $1.62 \times 10^{-6}$ | $2.28 \times 10^{-7}$ | $1.69 \times 10^{-7}$ | $1.04 \times 10^{-7}$ |
| $\frac{\Delta R}{R} / (C_0\Pi)$ (MPa/μM) | $7.14 \times 10^{-7}$ | $1.59 \times 10^{-5}$ | $3.06 \times 10^{-5}$ | $1.66 \times 10^{-5}$ | $7.60 \times 10^{-6}$ | $6.32 \times 10^{-6}$ |
| F(KHz) | 15.78 | 14.26 | 13.34 | 12.45 | 10.16 | 8.089 |

TABLE 10

Geometrical parameters for SCR modified C-shaped microcantilever

| Parameters | Nomenclature |
|---|---|
| Length of microcantilever L | L = 120 μm |
| Width of microcantilever W | W = 30 μm |
| Contacting beam | 30 × 12 μm² |
| Thickness of elliptical holes t | t = 1 μm |
| Transverse axis length of elliptical holes | $R_t$ = 5 μm |
| Longitudinal axis length of elliptical holes | $R_l$ = 15 μm |
| Distance between elliptical holes | $L_h$ = 15 μm |
| Distance between the first hole and the support | $L_d$ = 1 μm |

For the simulations whose results are presented below, the holes were moved towards the support, the distance between the holes was shortened, a large size, a large aspect ratio and a large depth for the holes was assumed. Table 11 provides these various parameters.

TABLE 11

Parameters for C-shaped microcantilevers

| Parameters | $R_l$ = 6 μm<br>$R_t$ = 2 μm<br>t = 1 μm | $R_l$ = 9 μm<br>$R_t$ = 3 μm<br>t = 1 μm | $R_l$ = 12 μm<br>$R_t$ = 4 μm<br>t = 1 μm |
|---|---|---|---|
| $\frac{\Delta R}{R}/(D\Pi)$ (MPa/Å) | $2.35 \times 10^{-7}$ | $3.77 \times 10^{-7}$ | $8.45 \times 10^{-7}$ |
| $\frac{\Delta R}{R}/(C_0\Pi)$ (MPa/μM) | $1.53 \times 10^{-5}$ | $5.82 \times 10^{-5}$ | $9.46 \times 10^{-5}$ |

Figure 28A:
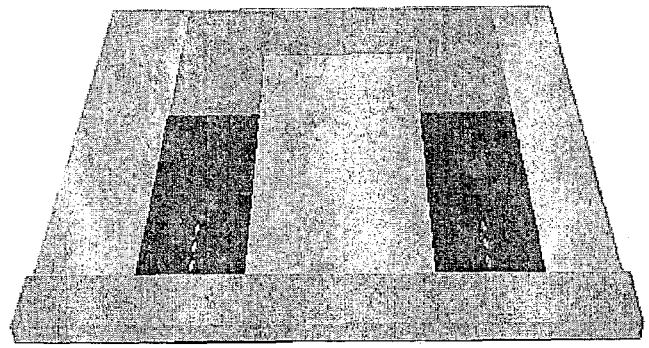
FIG. 28A shows an SCR C-shaped microcantilever.
Figure 28C:
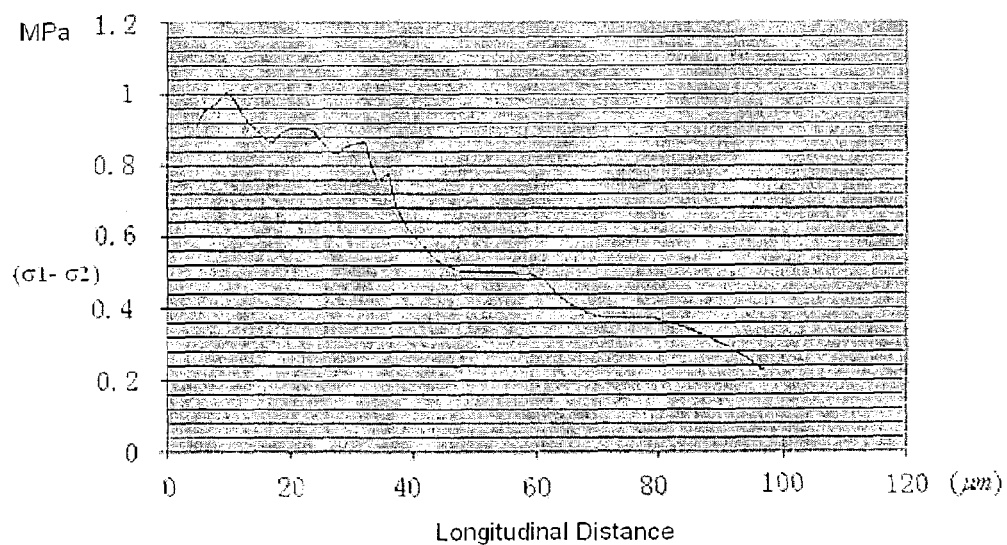
FIG. 28C shows the integrated differential stress along the longitudinal axis of an SCR C-shaped microcantilever.
Figure 28B:
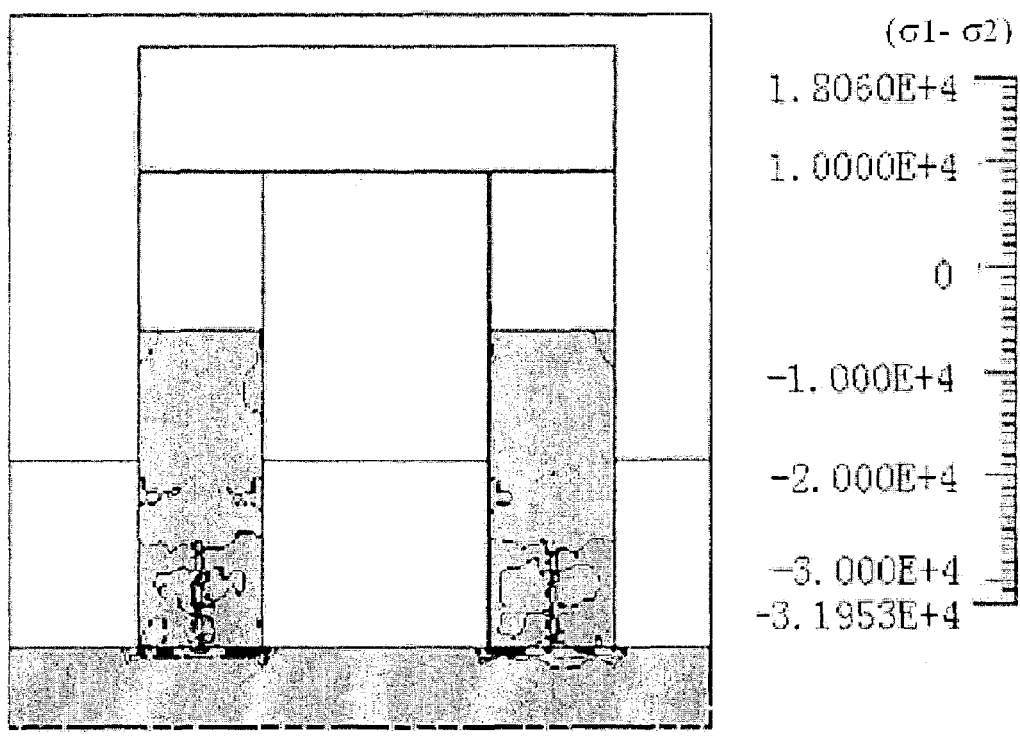
FIG. 28B shows the differential stress distribution of an SCR C-shaped microcantilever.

FIG. 28A shows the SCR modified C-shaped microcantilever. FIG. 28B shows the differential stress distribution and FIG. 28C shows the integrated differential stress along the longitudinal axis. As provided in FIG. 28C, the overlap of the three "peaks" and hence a comparatively stable flat roof area is found near the area where the ends of the microcantilever are attached to the solid support. Thus, in preferred embodiments of the present invention, a piezoresistive layer is in the area where the ends of the microcantilever are attached to the solid support in order to obtain large signals or measurements.

Resonance Frequency Shift

The resonance frequency shift of microcantilevers was examined using commercially available silicon microcantilevers from Thermomicroscopes, Inc., Sunnyvale, Calif. (Ultralevers™, types A, B, C and D), whose properties are provided in Table 12.

TABLE 12

Geometrical and physical parameters of the microcantilevers used in the experiments

| Type | L (μm) | W (μm) | Typical thickness (μm) | Typical force constant (N/m) | Typical resonance frequency (kHz) |
|---|---|---|---|---|---|
| UL20A | 180 | 25 | 1.8 | 1.9 | 53 |
| UL20B | 180 | 38 | 1.8 | 2.8 | 64 |
| UL20C | 85 | 18 | 1.8 | 13 | 300 |
| UL20D | 85 | 28 | 1.8 | 18 | 360 |

The changes in the resonance frequency of the microcantilevers were detected optically using an atomic force microscopy system (Autoprobe CP-Research™, Thermomicroscopes, Inc., Sunnyvale, Calif.). Microcantilevers were mounted to a cartridge with a piezoresistive film stack for operation in the non-contact or tapping mode. An optical detection system with a four-quadrant photodetector was used to detect the microcantilever detection and the resonance frequency. The ultralevers have a gold coating on the backside for enhanced surface reflectivity, which is also useful for chemical modification to obtain selective binding of specific analytes.

For the experiments described herein, self assembled monolayers (SAM) of aminoethanethiol and dodecanethiol were utilized as receptor molecules to modify the microcantilever surface. The sulfur group in the thiol chain has high affinity for binding to gold surfaces and hence well defined monolayers are generated, which are dense and stable. See Fritz, J., et al. (2000) Science 288:316-318, and Ulman, A. (1996) Chem. Rev. 96:1533-1554, which are herein incorporated by reference. Before chemically modifying the microcantilever, the microcantilever's frequency response (first order resonance) was measured using an Atomic Force Microscope (AFM) in the non-contact mode. Chemical modification was achieved by dipping the microcantilevers into saturated solutions of aminoethanethiol and dodecanethiol for a duration of 12 hours, followed by a 24 hour drying process. After that, the modified microcantilever's frequency response was recorded.

The height of the aminoethanethiol and dodecanethiol self assembled monolayers were taken to be 8 Å and 20 Å, respectively. Compared to the thickness of the microcantilever (1.8 μm), the SAMs are considered to be ultra thin films. See Moulin, A. M., et al. (2000) Ultramicroscopy 82:23-31, which is herein incorporated by reference. When a microcantilever is coated with a thin film, the flexural rigidity will change, and the change in stiffness as well as the mass will directly affect the resonance frequency of the microcantilever's vibration. The stiffness change will be reflected as a change in the force (cantilever bending) versus distance (scanner extension) curve of the microcantilever, which is directly obtained from AFM, and the slope of the linear portion of the curve is inversely proportional to the stiffness of the microcantilever.

The microcantilever was considered to be a long, thin section with one end fixed and the other end being free. Assuming the microcantilever behaves linearly elastic and uniform in dimension, and only a small deflection is issued, the resonance frequency of the microcantilever $\omega_n$ can be determined by Equation (28):

$$\omega_n = k_n^2 \sqrt{\frac{EI}{\lambda}} \tag{28}$$

wherein $k_n$ is constant,

EI is the flexural rigidity,

E is the elastic modulus,

I is the moment of inertia, and

λ is the linear density of the beam.

After the surface modifications, the characteristics of the microcantilever change due to the formation of the self assembled monolayer. The linear mass density of the modified microcantilever will become:

$$\lambda_c = \rho_s A_s + \rho_f A_f \quad (29)$$

and its flexural rigidity will be redefined as:

$$EI = E_s I_s + E_f I_f \quad (30)$$

wherein s represents the solid support that the microcantilever is fabricated to and f represents the self assembled monolayer.

In addition, the modified center of mass of the microcantilever is given by:

$$y_{cm} = \frac{E_s h_s^2 + E_f(2h_s h_f + h_f^2)}{2E_s h_s + 2E_s h_f} \quad (31)$$

The moment of inertia of the modified beam will also change to:

$$I_s = \frac{w h_s^3}{12} + w h_s \left( y_{cm} - \frac{h_s}{2} \right)^2 \quad (32)$$

$$I_f = \frac{w h_f^3}{12} + w h_f \left( \frac{h_f}{2} + h_s - y_{cm} \right)^2$$

Consequently, the new resonance frequency and the frequency shift are given by the following expressions:

$$\omega_c = k_n^2 \sqrt{\frac{E_s I_s + E_f I_f}{\lambda_c}} \quad (33)$$

$$\Delta \omega_c = k_n^2 \left[ \sqrt{\frac{E_s I_s + E_f I_f}{\lambda_c}} - \sqrt{\frac{EI}{\lambda}} \right]$$

Figure 29A:
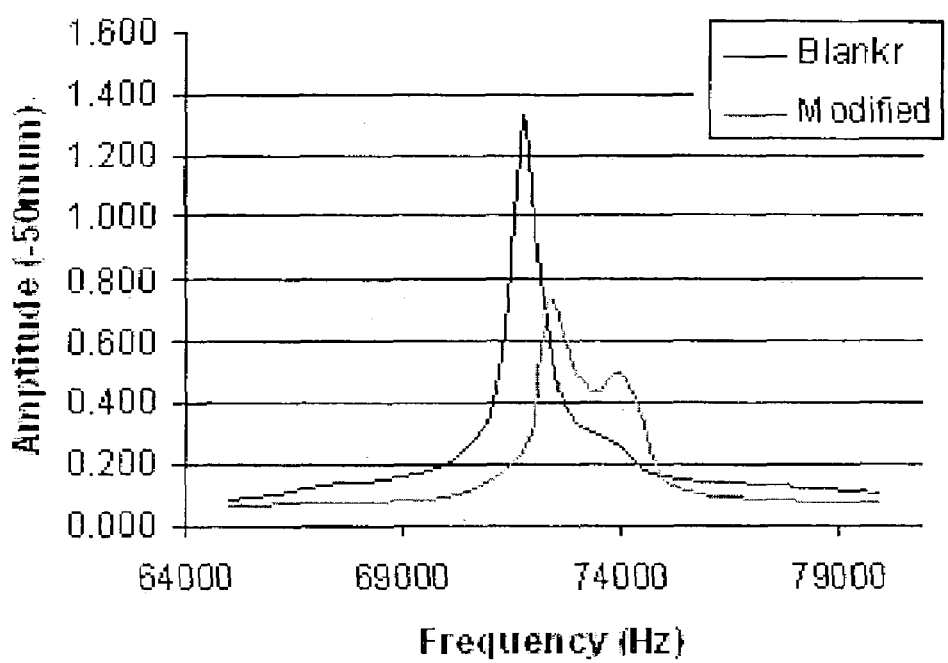
FIG. 29A shows the frequency response before and after modification for an aminoethanethiol SAM.
Figure 29B:
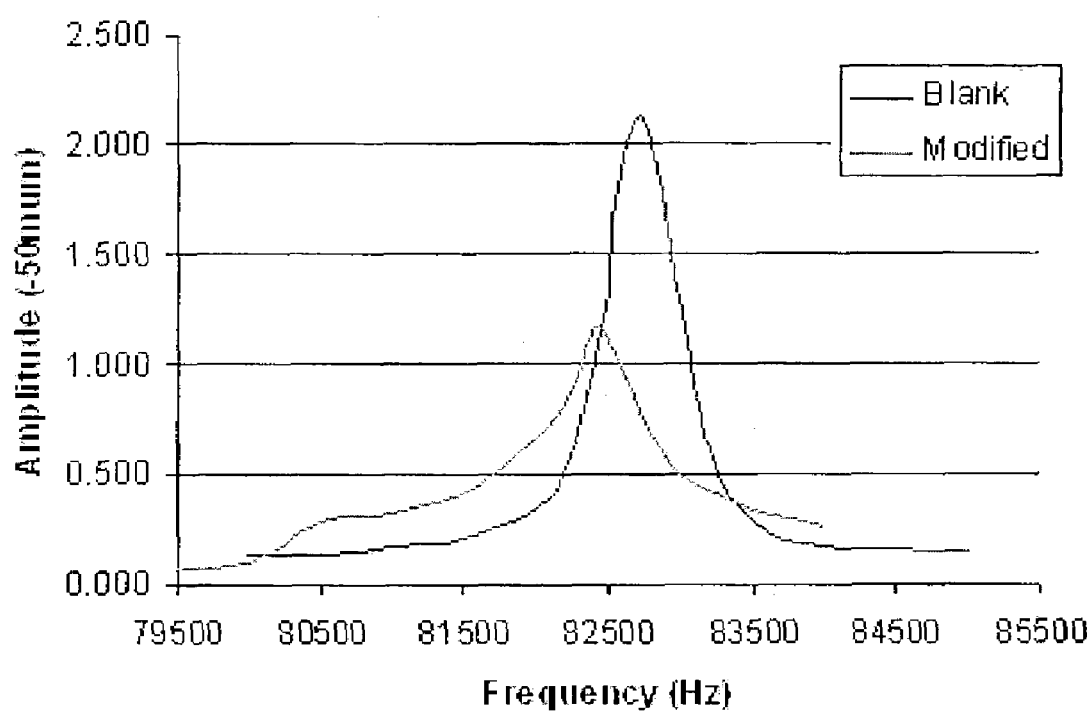
FIG. 29B shows the frequency response before and after modification for a dodecanethiol SAM.
Figure 30A:
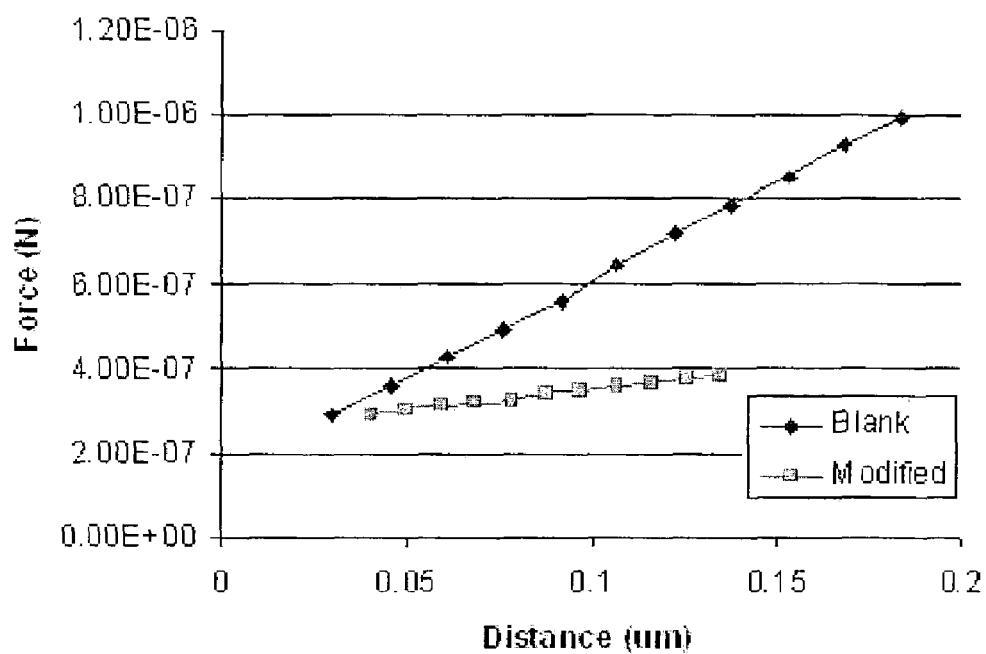
FIG. 30A shows force versus distance curves for aminoethanethiol coatings.
Figure 30B:
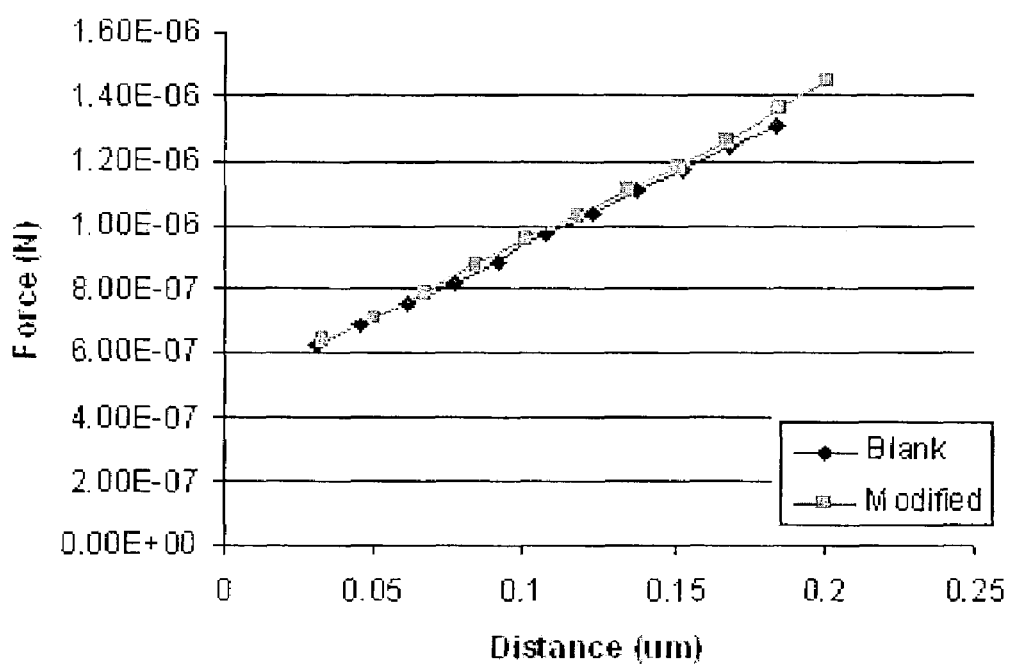
FIG. 30B shows force versus distance curves for dodecanethiol coatings.

These equations show that both the stiffness and the mass loading affect the resonance frequency of the microcantilever. See Lu, P., et al. (2001) Mater. Phys. Mench. 4:51-55, which is herein incorporated by reference. FIGS. 29A and 29B show the results of resonance frequency change measured using ultralevers of type B, as provided in Table 12, for aminoethanethiol and dodecanethiol coatings, respectively. For the case of aminoethanethiol coating in FIG. 29A, an increase in the resonance frequency was observed. However, the resonance frequency decreased for the dodecanethiol coating as shown in FIG. 29B. FIGS. 30A and 30B show the force versus deflection curves for aminoethanethiol and dodecanethiol, respectively. The stiffness of the microcantilever for aminoethanethiol increased and a small increase in the stiffness of the microcantilever for dodecanethiol was also observed.

An aminoethanethiol has a hydrochloride group at the end which leaves a proton upon salvation. The charged end of aminoethanethiol molecules can interact via van der Waals forces to form highly rigid three dimensional networks. In addition, the amino group of the molecule is oriented at a non-coplanar angle to the carbon backbone. Furthermore, dodecanethiol is a highly linear molecule and can form dense and pitless monolayers. Therefore, a self assembled monolayer of aminoethanethiol has a lower density compared to that of a dodecanethiol layer. Hence, the mass of the dense monolayer of dodecanethiol has a more dominant effect on the frequency shift: when the stiffness change for the microcantilever is negligible, mass loading dominates the shift in the resonance frequency of the microcantilever.

Fabrication of Microcantilevers

The microcantilevers of the present invention may be made by various methods known in the art as well as the methods provided herein. See e.g. Mechanical Microsensors (2001) ed. Elwenspoek and Wiegerink, Springer-Verlag Berlin Heidelberg, Germany; and The MEMS Handbook (2002) ed. Gad-el-Hak, CRC Press, Boca Raton, Fla., which are herein incorporated by reference. Further process optimization for fabrication may be employed to determine the performance and reliability of the methods. A key part of the process is the functionalization of the microcantilevers for specific receptor attachment. For ex situ testing of the microcantilevers, the fabricated microcantilevers will be mounted onto a conventional scanning probe microscope. The bi-medium/substrate will be placed under the microcantilever. For in situ experiments, the microcantilevers will be integrated into a microsensor such as a biochip.

Figure 31:
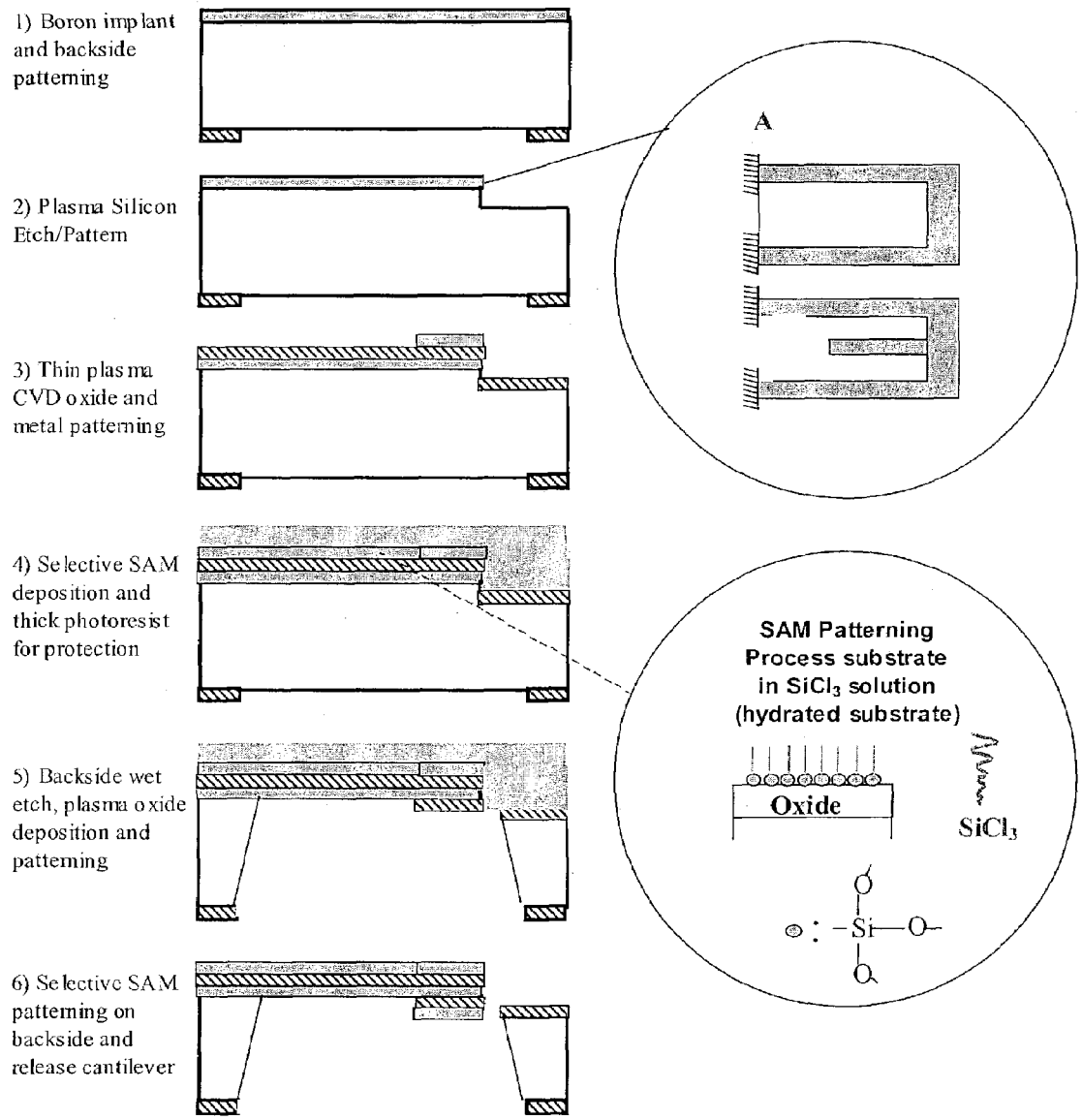
FIG. 31 is a schematic showing the fabrication of bimicrocantilevers and SAM functionalization, part A shows cantilevers of various structural shapes.

The microcantilevers of the present invention may be fabricated as illustrated in FIG. 31. The fabrication process for the microcantilever begins with oxide growth (dry oxidation, 1000 Å. The oxide is patterned on the backside to leave large openings. Next, the wafer is implanted with boron ($5 \times 10^{15-16}$ cm$^2$/sec, 150-160 KeV). The boron doped layer serves as an etch stop for patterning the microcantilever. After the implant, the wafer is annealed to drive-in the doping, preferably by rapid thermal processing (about 900-1000° C., about 15-30 seconds).

The next processing step depends on the specific biochemical functionalization of the microcantilever. For example, a self assembled monolayer (SAM) of SiCl$_3$ can be coated on hydrated surfaces, such as an oxide. Here, a plasma CVD oxide (1000 Å) layer and an aluminum metallization layer (1000 Å) are deposited and the metal layer is patterned to leave open spaces on the oxide for SAM patterning. Next, the top surface of the wafer is coated with a thick layer of resist for protection. After that, the backside of the wafer is wet etched in a solution of ethylene diamine pyrocatectol (EDP), which is a strong preferential etch for the <100> orientation compared to the <111> orientation. In addition, the boron doped layer will serve as an etch stop for the EDP etch. Boron doping is an effective etch stop when the doping concentration exceeds $5 \times 10^{19}$ atoms/cm$^3$, which reduces the etch rate by a factor of 50. The etch rate ratio for (100)/(111) is approximately equal to 35. Hence, the thickness and the stiffness of the microcantilever can be tailored through the doping parameters. After the EDP etch, plasma CVD oxide is deposited on the backside (1000 Å) and patterned. The oxide coated region on the backside is patterned with SAM and microcantilever fabrication is complete.

Functionalization of Microcantilevers with Receptors

Figure 32:
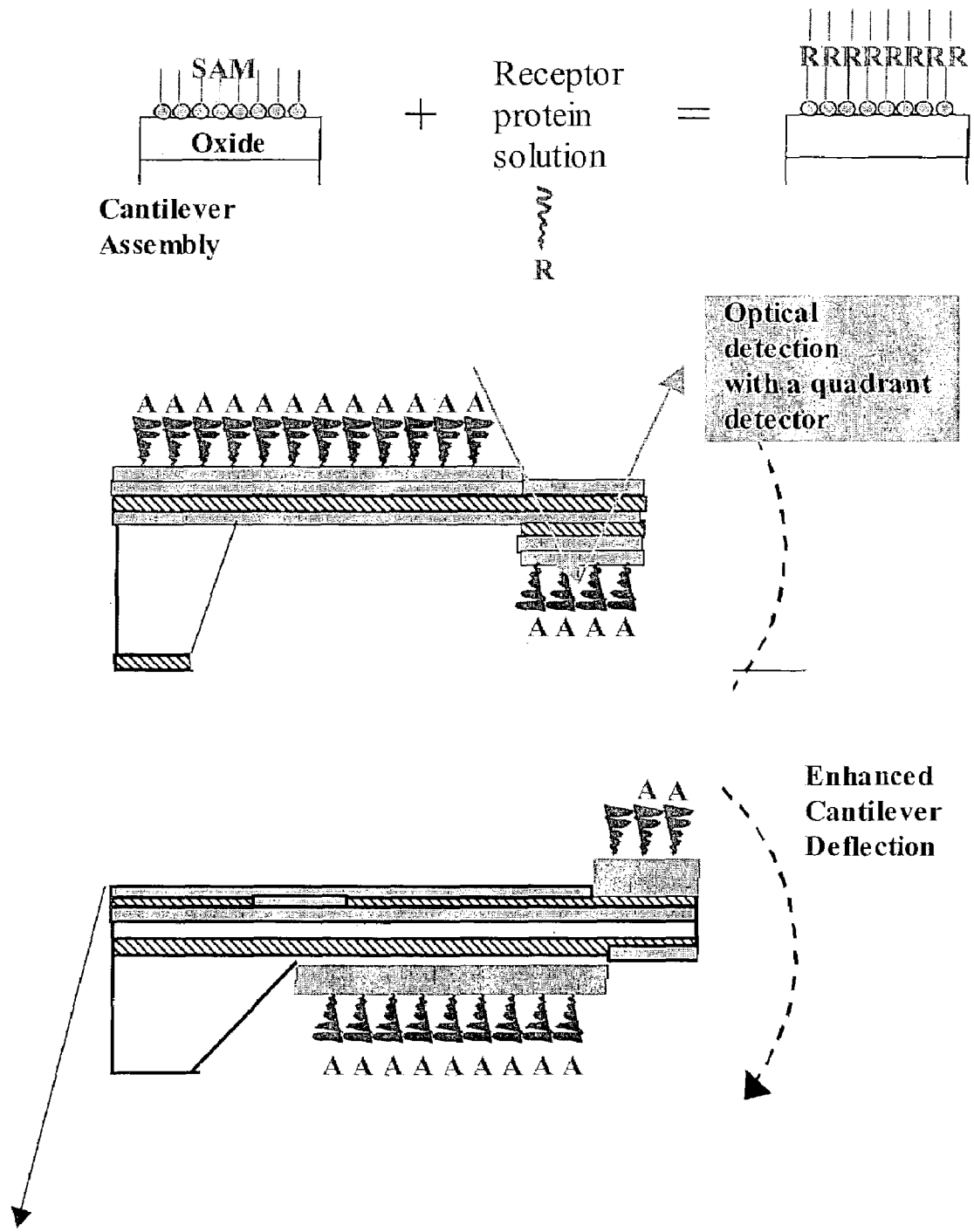
FIG. 32 shows bimicrocantilever detection schemes.

The microcantilevers of the present invention may be functionalized with receptors using a variety of methods known in the art. The receptors may be attached to the surface of the microcantilever simply by application in solution or suspension and drying. A liquid reaction medium can be applied to the surface, for example by flowing through the surface, by submerging the surface, or by applying a small volume to the surface. Removal of the excess liquid after an incubation period to allow the binding of the analyte to the receptor can be accomplished by any means known in the art, including gravity, vacuum, rinsing, and the like. In preferred embodiments, the microcantilevers can be dipped in a liquid suspension or solution of a desired receptor as provided in FIG. 32. Alternatively, the receptors may be immobilized to the surface of a microcantilever by avidin-biotin binding according to U.S. Pat. No. 6,235,488, which is herein incorporated by reference.

The microcantilever may be mounted or attached to a support such as an AFM head or a microsensor. The initial testing of the microcantilever may be conducted with a liquid cell arrangement, which is available with most AFM systems and known in the art.

Integration of Microcantilevers into Microsensors

As used herein, "microsensor" is used interchangeably with "microfluidic device" and refers to a device that may be used to assay at least one analyte in a fluid sample. The microsensors of the present invention comprise at least one microcantilever of the present invention. The microsensors and the microcantilevers of the present invention may made by micromachining. As used herein, "micromachining" and "microfabrication" refer to refer to any number of techniques which are useful in the generation of microstructures (structures with feature sizes of sub-millimeter scale). Such technologies include laser ablation, electrodeposition, physical and chemical vapor deposition, photolithography, wet chemical and dry-etching, injection molding, and LIGA (x-ray lithography, electrodeposition, and molding).

In some embodiments, an array of the microcantilevers of the present invention is integrated into a microsensor to assay certain analytes of interest. Each microcantilever in the microcantilever array may provide individual signal detection, i.e. each microcantilever provides an individual signal in response to a given analyte. Detection may be conducted using one of the various methods known in the art. Optical detection is preferred. Optical detection may be performed using a detector array of diode lasers or Vertical Cavity Surface Emitting Lasers (VCSEL) as shown in FIG. 33. A detector array individually samples the microcantilever deflections upon the binding or interaction with given analytes.

Detection of the analytes may be based on two different strategies. The first strategy is based upon the complexing of a given analyte to a given receptor immobilized on the microcantilever surface. For non-piezoresistive microcantilevers, the microcantilever deflects when the analyte is complexed with the receptor and the amount of deflection is correlated to the quantity of the given analyte. The measured quantity may be averaged over several microcantilevers for statistical significance. In addition, parallel detection studies may be conducted for analyzing multiple samples concurrently. For piezoresistive microcantilevers, off-chip detection is not necessary and microcantilever deflection may be measured through monitoring the change in piezoresistivity.

The second strategy is based upon the resonance frequency of the microcantilevers. Resonance frequency may be measured using a variety of methods known in the art. Generally, resonance frequency is measured with the microfluidic chamber empty and then the chambers are filled with the sample to be tested. Next, the chambers are emptied and the resonance frequency is again measured. The change in the resonance frequency is indicative of a given analyte complexed with a given receptor immobilized on the microcantilever surface.

Figure 33A:
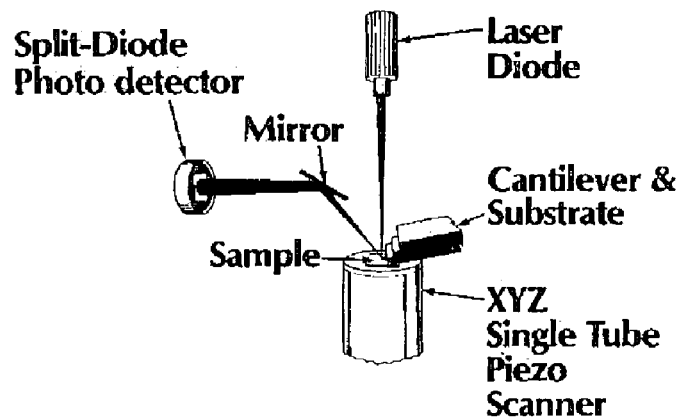
FIG. 33A shows a device for detecting an analyte in a sample using a microcantilever of the present invention.
Figure 33B:
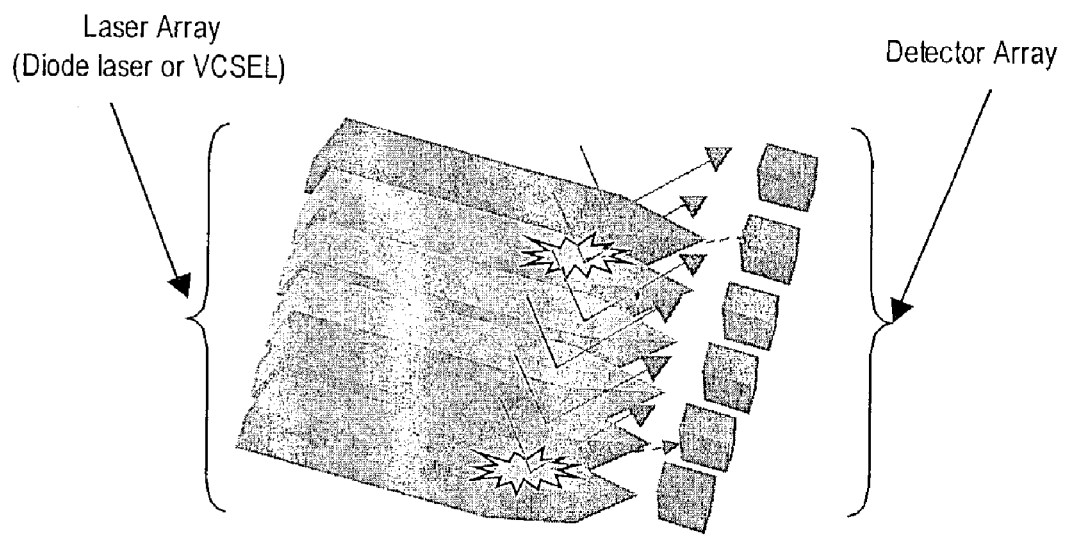
FIG. 33B shows a multiple microcantilever detection scheme.
Figure 33C:
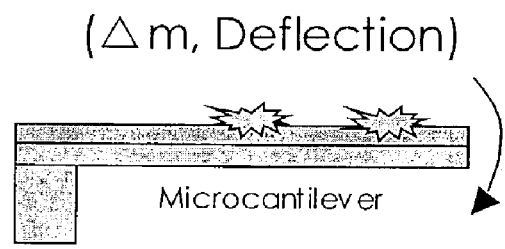
FIG. 33C is a schematic of the principle of AFM operation.
Figure 33D:
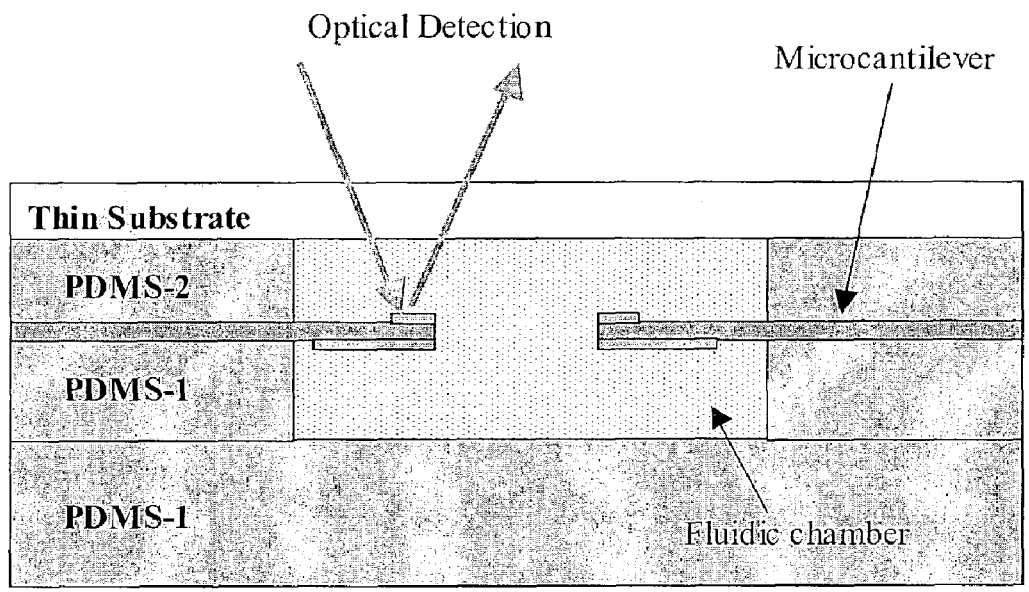
FIG. 33D shows a microfluidic device or a microsensor having a microcantilever.
Figure 34A:
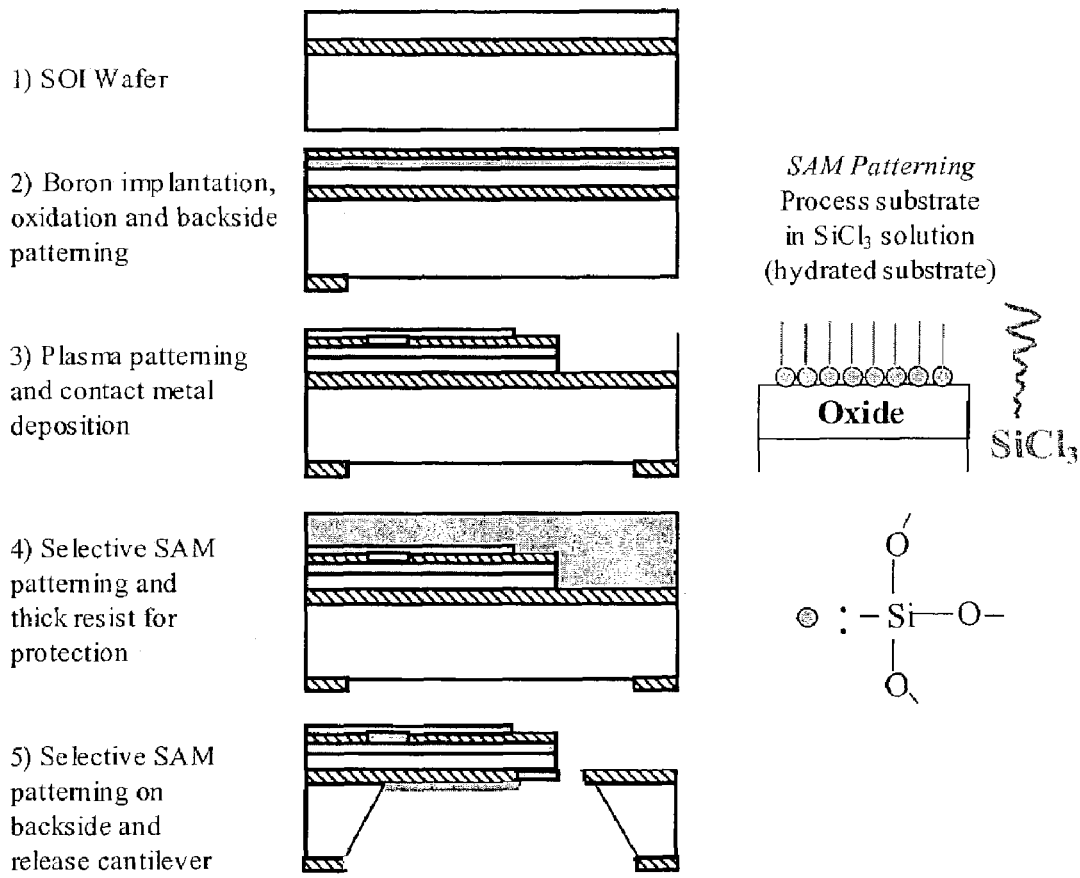
FIG. 34A is a schematic of the processing steps for fabrication and functionalization of the microcantilevers of the present invention.
Figure 34B:
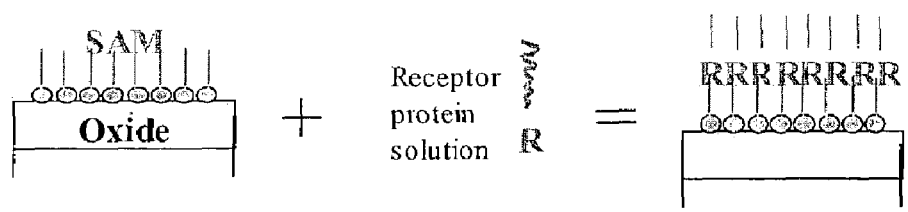
FIG. 34B is a schematic of a microfluidic device having a (piezoresistive) microcantilever of the present invention.
Figure 34C:
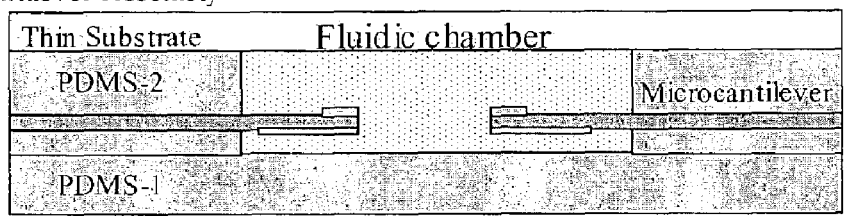

The microcantilevers of the present invention may be integrated into a microfluidic device such as that schematically shown in FIG. 33A. The microfluidic device generally comprises at least one receptor immobilized on at least one microcantilever and a detector such as the detector array shown in FIG. 33B that detects the change in the microcantilever when a ligand complexes with the receptor that is immobilized on its surface. The microfluidic device also contains a solid support to which the microcantilevers are attached. The microfluidic device may further contain at least one microfluidic channel through which the fluid sample to be tested flows. As used herein, "microfluidic channel" is used interchangeably with "microchannel" to refer to a channel of sufficient size to allow fluid flow, preferably a channel generally in the form of a tube that has mean cross-sectional measurement of about 3 mm or less, preferably about 2 mm to about 1 mm or less, preferably about 0.5 mm or less, more preferably about 100 µm or less, preferably about 10 µm or less, even more preferably about 100 µm or less, still more preferably about 80 nm or less, or about 60 nm or less, or about 40 nm or less, or about 20 nm or less. The microcantilevers may be placed in the microfluidic channels or the microcantilevers may be placed in microfluidic cells or chambers.

The solid support is preferably made of a substrate that is suitable for micromachining or microfabrication. In preferred embodiments, the substrate is optically transparent. Suitable substrates include silicon, silica, quartz, glass, controlled pore glass, carbon, alumina, titania, tantalum oxide, germanium, silicon nitride, zeolites, gallium arsenide, gold, platinum, aluminum, copper, titanium, polystyrene; poly(tetra)fluoroethylene (PTFE); polyvinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PMI); polyalkenesulfone (PAS); polypropylene; polyethylene; polyhydroxyethylmethacrylate (HEMA); polydimethylsiloxane (PDMS); polyacrylamide; polyimide; and block-copolymers, and the like, and combinations thereof. In preferred embodiments, the substrate is transparent, thereby allowing optical detection.

The microfluidic channels may be made using methods known in the art. For example, the microfluidic channels can be formed on the surface of the substrate by either (1) bulk micromachining, (2) sacrificial micromachining, (3) LIGA (high aspect ratio plating) or (4) other techniques known in the art, or any combination thereof. Such techniques are well known in the semiconductor and microelectronics industries and are described in, for example, Ghandi, VLSI Fabrication Principles, Wiley (1983) and Sze, VLSI Technology, 2nd Ed., McGraw-Hill (1988); Wolf and Taube, Silicon Processing for the VLSI Era, Vol. 1, Lattice Press (1986), and Madou, Fundamentals of Microfabrication, CRC Press (1997); which are herein incorporated by reference.

In bulk micromachining, large portions of the substrate are removed to form rectangular or v-shaped grooves comprising the final dimensions of the microfluidic channels. This process is usually carried out with standard photolithographic techniques involving spin-coating of resist materials, illumination through lithography masks followed by wet-chemical development and posttreatment steps such as descumming and post-baking. The resulting resist pattern is then used as an etch resist material for subsequent wet or dry etching of the bulk material to form the desired topographical structures. Typical resist materials include positive and negative organic resists (such as Kodak 747, PR102), inorganic materials (such as polysilicon, silicon nitride) and biological etch resists (for example Langmuir-Blodgett films and two-dimensional protein crystals such as the S-layer of *Sulfolobus acidocladarius*). Pattern transfer into the substrate and resist stripping occurs via wet-chemical and dry etching techniques including plasma etching, reactive ion etching, sputtering, ion-beam-assisted chemical etching and reactive ion beam etching.

In sacrificial micromachining, the substrate is left essentially untouched. Various thick layers of other materials are built up by vapor deposition, plasma-enhanced chemical vapor deposition (PECVD) or spin coating and selectively remain behind or are removed by subsequent processing steps. Thus, the resulting channel walls are chemically different from the bottom of the channels and the resist material remains as part of the microdevice. Typical resist materials for sacrificial micromachining are silicon nitride ($Si_3N_4$), polysilicon, thermally grown silicon oxide and organic resists such as SU-8 and polyimides allowing the formation of high aspect-ratio features with straight sidewalls.

In high-aspect ratio plating or LIGA, three-dimensional metal structures are made by high-energy X-ray radiation exposures on materials coated with X-ray resists. Subsequent electrodeposition and resist removal result in metal structures that can be used for precision plastic injection molding. These injection-molded plastic parts can be used either as the final microdevice or as lost molds. The LIGA process has been described by Becker et al., (1986) Microelectron Engineering 4:35-56 and Becker et al., (1982) Naturwissenschaften 69:520-523, which are herein incorporated by reference.

Alternative techniques for the fabrication of microchannel arrays include focused ion-beam (FIB) milling, electrostatic discharge machining (EDM), ultrasonic drilling, laser ablation (U.S. Pat. No. 5,571,410, which is herein incorporated by reference), mechanical milling and thermal molding techniques. One skilled in the art will recognize that many variations in microfabrication or micromachining techniques may be used to construct the device of the present invention.

A transparent or translucent cover may be attached to the substrate via anodic bonding or adhesive coatings to provide microfluidic channels that have inlet and outlet ports. In preferred embodiments, the covers are glass, especially Pyrex or quartz glass. In alternative embodiments, a cover which is neither transparent nor translucent may be bonded or otherwise attached to the substrate to enclose the microchannels. In other embodiments the cover may be part of a detection system to monitor the interaction between receptors immobilized on the microcantilevers and given analytes. Alternatively, a polymeric cover may be attached to a polymeric substrate channel array by other means, such as by the application of heat with pressure or through solvent-based bonding.

The volume of each enclosed microfluidic channel may optionally be from about 5 nanoliters to about 300 nanoliters. In preferred embodiments, the volume of an enclosed microfluidic channels are between about 10 and about 50 nanoliters. Volumes of fluid may be moved through the microfluidic channels using methods known in the art. In some embodiments of the present invention, bulk-loading dispensing devices can be used to load all microfluidic channels of the device at once with the same sample. Alternatively, integrated microcapillary dispensing devices may be microfabricated out of glass or other substrates to load fluids separately to each microfluidic channel of the device.

In some embodiments, an inverse layout of the microfluidic channel patterns may be generated using known photolithography techniques with a thick negative UV photoresist on silicon wafers, and then PDMS is molded over to generate the microfluidic channel patterns. After curing, the PDMS layer is peeled off from the silicon master. The fabricated microcantilevers will be placed over the cavities and a second PDMS layer will be used to fix the positions of the microcantilevers. Finally, to seal the fluidic channel structures, the biochip is bonded to a substrate such as a thin glass slide.

After formation of the microfluidic channels, the sides, bottom, or cover of the microfluidic channels or any portion or combination thereof, can then be further chemically modified to achieve desired bioreactive and biocompatible properties.

In some embodiments, the microfluidic device may further comprise at least one chamber wherein the sample to be tested can be processed or chemically modified prior to contact with the microcantilevers. In other embodiments, the microfluidic device comprises at least one chamber that contains reagents, such as buffers and enzymes, that are necessary for the assay being conducted.

In some embodiments, the microcantilevers of the present invention may be used in a palette of cantilever array blocks such as those described in U.S. Patent Application 20020102743, which is herein incorporated by reference.

Photomechanical Effects

Analyte molecules on the receptor surface of an ordinary microcantilever usually absorb incident photons within a certain range of wavelengths from a laser source or infrared radiations from a spectrometer. See Datskos, P. G., et al. (2001) Photo-Mechanical Chemical Microsensors, Sensors and Actuators B, 76:393-402, which is herein incorporated by reference. Accordingly, the analyte molecules will have higher vibrational levels and internal energies. The internal energy is dissipated on the surface of the microcantilever by conduction. Therefore, the surface temperature will increase which will cause an increase in bimetallic effects. Photon-analyte interactions cause increased deflections which cause the microcantilevers to have higher sensitivities even for small analyte concentrations. Thus, the present invention also provides microcantilevers that are optimized for photon-analyte interactions.

Exterior Mass Loading Effects

The present invention also provides assay methods and systems wherein nanostructures which include nanobeads, nanodots, nanocrystals, quantum dots, and quantum beads, coated with a given receptor that specifically binds to given analytes that are complexed with receptors immobilized on the microcantilever are injected after the test sample passes the microcantilever. The nanostructures bound to the analyte/receptor complex will increase the deflection of the microcantilever, thereby increasing accuracy and sensitivity.

The nanostructures may further include receptors that specifically bind a given ligand that is contacted with the nanostructures after the nanostructures are attached to the analyte/receptor complexes on the microcantilever surface in order to provide an even more amplified deflection. In alternative embodiments, the nanostructures may be electrically charged. Electrically charged nanostructures bound to the analyte/receptor complex on the microcantilever will, in essence, provide an electrically charged microcantilever. The deflections of the electrically charged microcantilever can be enhanced or magnified by exposure to electrical forces.

Multiple Microcantilevers with Signal Processing

Multiple microcantilever arrangements can be employed with integrated signal processing which would reduce the noise level in the analysis.

Geometrical Improvements

Turbulence in fluid samples affects the way a microcantilever deflects, such as lateral or torsional displacements. As a result, vertical deflection and detection is adversely affected. Additional piezoresistive elements can be integrated onto the microcantilevers, which would be used to calculate the torsional and lateral displacements; hence corrections can be made in the vertical displacement profile.

Flow Requirements

Although turbulence in fluid samples affect accuracy of detection, in some situations the turbulence causes a mixing effect that increases the number of analytes that interact or bind with the receptors immobilized on the microcantilevers which reduces drift effects.

Initial Conditions of Microcantilevers

Due to the bimaterial (such as Au and Si) effects, the slight temperature difference between the test sample and the buffer in the microfluidic cells containing the microcantilevers may cause deflections in the microcantilevers prior to the interaction of the analytes with the receptors immobilized on the microcantilevers. See Fritz, J., et al. (2000) Science 288:316-318, which is herein incorporated by reference. Although control or reference microcantilevers (having no immobilized receptors or do not bind analytes) may be used to account for some biomaterial effects, temperature differences and nonspecific binding, microcantilevers are not physically identical, and therefore deflections of control microcantilevers may not provide an accurate accounting.

Therefore, in preferred embodiments, bimaterial effects are minimized by controlling the temperature of the microfluidic cells containing the microcantilevers with thermoelectric coolers. See Wu, G., et al. (2001) PNAS USA 98:1560-1564, which is herein incorporated by reference. In addition, the arrival of the sample in the microfluidic cell may be delayed to allow the temperature of the sample to near or reach the temperature of the buffer in the microfluidic cell, thereby reducing the deflections due to temperature differences. The sample may be delayed using physical, mechanical, electrical, thermal, and magnetic methods. For example, the sample may be delayed by using a filter that slows down the flow of the sample into a microfluidic channel. The sample may be delayed by having to pass through a microfluidic channel that is long and has a numerous turns before reaching the microcantilevers or the microfluidic cell containing the microcantilevers. The sample may be delayed by using electrical or magnetic force fields in a manner similar in concept to those applied, in minigels for protein and nucleic acid assays. The sample may be delayed with a porous medium with large effective thermal conductivity in the flow passage.

Drift of Microcantilevers

When a microcantilever is enclosed in a fluid environment, a long-term drift which affects the deflection of the microcantilever occurs. See Raiteri, R., et al. (2000) Electrochimica Acta 46:157-163, which is herein incorporated by reference. This long-term drift is due to changes to the surfaces of the microcantilever as a result of thermal effects such as those discussed previously and chemical effects. As for the chemical effects, significant deflections have been observed when the microcantilever is immersed in a fluid environment irrespective of whether the microcantilever is a bimaterial or a single material. See Moulin, A. M., et al. (2000) Ultramicroscopy 82:23-31, which is herein incorporated by reference. These deflections occur because the adsorbed surface species re-equilibrate in contact with the ionic buffer and these cause surface stresses. As a result, unwanted microcantilever deflections occur. Therefore, the present invention provides methods and systems wherein the microcantilevers are allowed to equilibrate (for up to about one or more hours, preferably about two to about three hours) prior to the introduction of the sample.

Biostatic Microsensor

The present invention also provides biostatic microsensors which comprise a given receptor joined to a support such as a silicon wafer. An analyte complexed with the receptor results in a restrained deflection upon which the surface of the support will become stressed or relieved. The photon absorption properties of the surface change according to the presence or absence of surface stresses. The reflected photon intensity from the surface may be measured by an infrared receiver. This intensity may then be correlated to the analyte concentration.

Nanostructures

The microcantilever deflections may be enhanced by increasing the functionalized surface area of the microcantilevers. The functionalized surface area may be increased by incorporating nanostructures such as quantum dots, nanotubes, nanobeads, colloids, porous polysilicon layers, and the like on the surface. An array of microcantilevers may also be used in the biochips of the present invention.

Carbon nanotubes, are nanostructures made of trigonally-hybridized carbon with a diameter of a few nanometers and a length of many micrometers. Carbon nanotubes are strong, flexible, and have electronic properties ranging from semiconducting to metallic and can be functionalized with different molecules. Various types of biomolecules such as proteins and enzymes can be encapsulated within or immobilized on the surface of carbons nanotubes. The electronic properties of nanotubes may be coupled with the specific binding ability of biomolecules and used in accordance with the present invention. For example, the microsensors of the present invention may comprise microelectrodes made out of an array of carbon nanotubes having given enzymes encapsulated or attached thereto.

Nanotubes may be grown, aligned, or patterned on given substrates using methods known in the art. Preferred methods for fabricating aligned carbon nanotubes are those in which the alignment is induced during growth. Micropatterns of aligned nanotubes perpendicular to the substrate surface have also been prepared by masking techniques or by pre-patterning the substrate using e-beam lithography or soft-lithography. Also, carbon nanotubes can be grown on one side of the microcantilever (vertically), and the ends of the tubes can be functionalized so that they can interact or bind with given ligands. See U.S. Patent Application No. 20020172963, which is herein incorporated by reference.

In some embodiments of the present invention, given receptors may be immobilized on nanotubes attached to a microcantilever only. In other embodiments, the receptors may be immobilized on both the nanotubes and the microcantilever. The receptors immobilized on the nanotubes may be the same or different from the receptors immobilized on the microcantilever.

In preferred embodiments of the present invention, patterns of aligned nanotubes are grown on one side of a microcantilever using chemical vapor deposition (CVD) methods known in the art to grow the nanotubes.

Figure 35A:
FIG. 35A is an electron micrograph showing nanotubes on a microcantilever of the present invention.
Figure 35B:
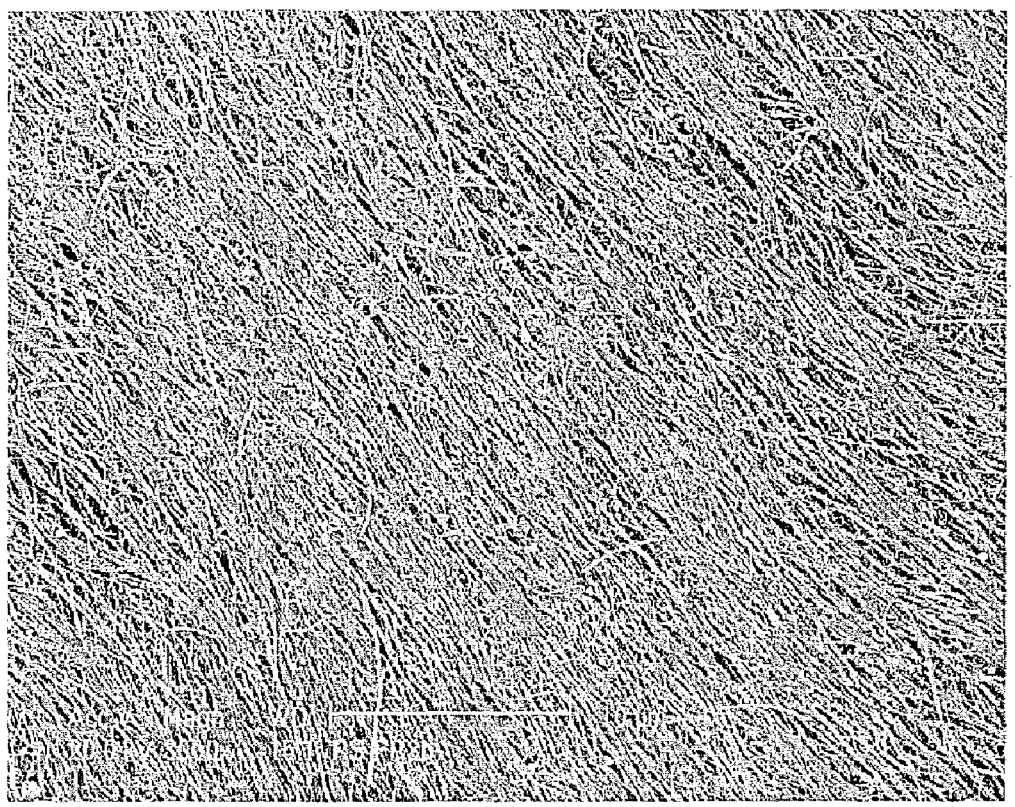
FIG. 35B is an electron micrograph showing nanotubes on a microcantilever of the present invention.

Micrographs of aligned patterns of nanotubes using CVD of ferrocene are shown in FIGS. 35A and 35B. CVD pyrolysis of a suitable precursor may be used for large area and controlled growth of carbon nanotubes. In some embodiments, the nanotubes may be grown in a specific pattern on a substrate or microcantilever to increase the functionality and versatility of microcantilevers and microsensors.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A microcantilever comprising a first section and a second section attached to a solid support, and the first section and the second section are further attached to each other to form a long slit therebetween having a width, wherein the first section has a top surface and a bottom surface and the second section has a top surface and a bottom surface, and at least one receptor is immobilized on the top surface of the first section and at least one receptor is immobilized the bottom surface of the second section.

2. The microcantilever of claim 1, wherein a ligand complexed with the receptor provides a change in the width of the long slit or its area.

3. The microcantilever of claim 1, further comprising a piezoresistive layer on the surface of the first and second sections of the microcantilever, wherein a ligand complexed with the receptor provides a change in piezoresistivity.

4. The microcantilever of claim 3, wherein the microcantilever has a first end and a second end and the first end is attached to said solid support, and the piezoresistive layer is located on the microcantilever in an area closer to the first end than the second end.

5. The microcantilever of claim 3, wherein the microcantilever comprises at least one stress concentrated region.

6. The microcantilever of claim 5, wherein the stress concentrated region is the result of at least one hole in the microcantilever.

7. The microcantilever of claim 3, wherein the microcantilever has a first end and a second end and the first end is attached to said solid support, and said hole is located in an area closer to the first end than the second end.

8. The microcantilever of claim 1, wherein the width allows photons to pass through the long slit.

9. The microcantilever of claim 1, further comprising at least one nanostructure attached thereto.

10. The microcantilever of claim 9, wherein the nanostructure is a nanotube, a nanobead, a nanocrystal, a quantum bead, a quantum dot, or a colloid.

11. The microcantilever of claim 9, wherein the nanostructure is functionalized.

12. A device comprising at least one microcantilever of claim 1.

13. The device of claim 12, wherein the device comprises a plurality of microcantilevers.

14. The device of claim 12, further comprising at least one microchannel through which a fluid sample may flow.

15. The device of claim 12, further comprising at least one chamber.

16. The device of claim 12, wherein the microcantilever is located within the chamber.

17. The device of claim 15, wherein the chamber comprises at least one reagent required for detecting or measuring the ligand.

18. A method for assaying at least one analyte in a sample which comprises exposing the microcantilever of claim 1 to the sample, and
detecting or measuring the change in the width of the slit or its area or a change in the piezoresitivity of a piezoresistive layer located on the microcantilever.

19. The method of claim 18, wherein the analyte is a chemical agent or a biological agent.

20. The method of claim 19, wherein the chemical agent is an insecticide, a pesticide, a herbicide, tabun, sarin, soman, methylphosphonothioic acid, sulphur mustard, nitrogen mustard, lewisite, phosgene oximine, phosgene, diphosgene, chloropicrin, or an organophosphate compound.

21. The method of claim 19, wherein the biological agent is a cellular receptor, a peptide, a polypeptide, a protein, an antibody, an antigen, a polynucleotide, a polysaccharide, a lipid, a steroid, a prostaglandin, a toxin, or a prostacycline.

22. The method of claim 21, wherein the toxin is a botulinum toxin, a ricin toxin, a saxitoxin, an enterotoxin, an exotoxin, a mycotoxin, or a neurotoxin.

23. The method of claim 19, wherein the biological agent is a marker for *Bacillus, Mycobacterium, Francisella, Brucella, Clostridium, Yersinia, Variola, Orthopox,* or *Burkholderia*, a virus that causes Congo-Crimean hemorrhagic fever (CCHF), Ebola Haemorrhagic Fever, Rift Valley Fever (RVF), smallpox, or Venezuelan equine encephalitis (VEE).

24. The method of claim 18, wherein the sample is a liquid, a suspension, or a gas.

25. The method of claim 18, further comprising the step of contacting the microcantilever with at least one nanostructure comprising at least one or more additional receptors specific for the analyte complexed to the immobilized receptor on the microcantilever.

26. A microcantilever comprising a first section and a second section attached to a solid support, and the first section and the second section are attached to each other at both ends to form a long slit therebetween having a width, wherein the first section has a top surface and a bottom surface and the second section has a top surface and a bottom surface, and at least one receptor is immobilized on the top surface of the first section and at least one receptor is immobilized the bottom surface of the second section.

27. The microcantilever of claim 26, wherein a ligand complexed with the receptor provides a change in the width of the long slit or its area.

28. The microcantilever of claim 26, further comprising a piezoresistive layer on the surface of the first and second sections of the microcantilever, wherein a ligand complexed with the receptor provides a change in piezoresistivity.

29. The microcantilever of claim 28, wherein the microcantilever has a first end and a second end and the first end is attached to said solid support, and the piezoresistive layer is located on the microcantilever in an area closer to the first end than the second end.

30. The microcantilever of claim 28, wherein the microcantilever comprises at least one stress concentrated region.

31. The microcantilever of claim 30, wherein the stress concentrated region is the result of at least one hole in the microcantilever.

32. The microcantilever of claim 30, wherein the microcantilever has a first end and a second end and the first end is attached to said solid support, and said hole is located in an area closer to the first end than the second end.

33. The microcantilever of claim 26, wherein the width allows photons to pass through the long slit.

34. The microcantilever of claim 26, further comprising at least one nanostructure attached thereto.

35. The microcantilever of claim 34, wherein the nanostructure is a nanotube, a nanobead, a nanocrystal, a quantum bead, a quantum dot, or a colloid.

36. The microcantilever of claim 26, wherein the nanostructure is functionalized.

37. A device comprising at least one microcantilever of claim 26.

38. The device of claim 37, wherein the device comprises a plurality of microcantilevers.

39. The device of claim 37, further comprising at least one microchannel through which a fluid sample may flow.

40. The device of claim 37, further comprising at least one chamber.

41. The device of claim 12, wherein the microcantilever is located within the chamber.

42. The device of claim 40, wherein the chamber comprises at least one reagent required for detecting or measuring the ligand.

43. A method for assaying at least one analyte in a sample which comprises exposing the microcantilever of claim 26 to the sample, and
detecting or measuring the change in the width of the slit or its area or a change in the piezoresitivity of a piezoresistive layer located on the microcantilever.

44. The method of claim 43, wherein the analyte is a chemical agent or a biological agent.

45. The method of claim 44, wherein the chemical agent is an insecticide, a pesticide, a herbicide, tabun, sarin, soman, methylphosphonothioic acid, sulphur mustard, nitrogen mustard, lewisite, phosgene oximine, phosgene, diphosgene, chloropicrin, or an organophosphate compound.

46. The method of claim 44, wherein the biological agent is a cellular receptor, a peptide, a polypeptide, a protein, an antibody, an antigen, a polynucleotide, a polysaccharide, a lipid, a steroid, a prostaglandin, a toxin, or a prostacycline.

47. The method of claim 46, wherein the toxin is a botulinum toxin, a ricin toxin, a saxitoxin, an enterotoxin, an exotoxin, a mycotoxin, or a neurotoxin.

48. The method of claim 44, wherein the biological agent is a marker for *Bacillus, Mycobacterium, Francisella, Brucella, Clostridium, Yersinia, Variola, Orthopox,* or *Burkholderia*, a virus that causes Congo-Crimean hemorrhagic fever (CCHF), Ebola Haemorrhagic Fever, Rift Valley Fever (RVF), smallpox, or Venezuelan equine encephalitis (VEE).

49. The method of claim 43, wherein the sample is a liquid, a suspension, or a gas.

50. The method of claim 43, further comprising the step of contacting the microcantilever with at least one nanostructure comprising at least one or more additional receptors specific for the analyte complexed to the immobilized receptor on the microcantilever.

51. A microcantilever having a first section having a free end and an end attached to a solid support, and a second section having a free end and an end attached to said support at a distance directly under the first section in a plane parallel to the plane of the first section, wherein the first and second sections have top and bottom surfaces, and at least one receptor is immobilized to the top surface of the first section and at least one receptor is immobilized to the bottom surface of the second section, and wherein the first and second sections are linked together only at the ends attached to the solid support.

52. The microcantilever of claim 51, wherein a ligand complexed with the receptor provides a change in the distance between the free ends of the first and second sections.

53. The microcantilever of claim 51, further comprising at least one nanostructure attached thereto.

54. The microcantilever of claim 53, wherein the nanostructure is a nanotube, a nanobead, a nanocrystal, a quantum bead, a quantum dot, or a colloid.

55. The microcantilever of claim 53, wherein the nanostructure is functionalized.

56. A device comprising at least one microcantilever of claim 51.

57. The device of claim 56, wherein the device comprises a plurality of microcantilevers.

58. The device of claim 56, further comprising at least one microchannel through which a fluid sample may flow.

59. The device of claim 56, further comprising at least one chamber.

60. The device of claim 59, wherein the microcantilever is located within the chamber.

61. The device of claim 59, wherein the chamber comprises at least one reagent required for detecting or measuring the ligand.

62. A method for assaying at least one analyte in a fluid sample which comprises
exposing a microcantilever of claim 51 to the fluid sample, and
detecting or measuring a change in the distance between the free ends of the first and second sections.

63. The method of claim 62, wherein the analyte is a chemical agent or a biological agent.

64. The method of claim 63, wherein the chemical agent is an insecticide, a pesticide, a herbicide, tabun, sarin, soman, methylphosphonothioic acid, sulphur mustard, nitrogen mustard, lewisite, phosgene oximine, phosgene, diphosgene, chloropicrin, or an organophosphate compound.

65. The method of claim 63, wherein the biological agent is a cellular receptor, a peptide, a polypeptide, a protein, an antibody, an antigen, a polynucleotide, a polysaccharide, a lipid, a steroid, a prostaglandin, a toxin, or a prostacycline.

66. The method of claim 62, further comprising the step of contacting the microcantilever with at least one nanostructure comprising at least one or more additional receptors specific for the analyte complexed to the immobilized receptor on the microcantilever.

* * * * *